US007869879B2

(12) United States Patent
Errico et al.

(10) Patent No.: US 7,869,879 B2
(45) Date of Patent: *Jan. 11, 2011

(54) ELECTRICAL STIMULATION TREATMENT OF HYPOTENSION

(75) Inventors: Joseph P. Errico, Warren, NJ (US); Steven Mendez, New York, NY (US); James R. Pastena, Succasunna, NJ (US)

(73) Assignee: ElectroCore LLC, Morris Plains, NJ (US)

( * ) Notice: Subject to any disclaimer, the term of this patent is extended or adjusted under 35 U.S.C. 154(b) by 50 days.

This patent is subject to a terminal disclaimer.

(21) Appl. No.: 12/506,297

(22) Filed: Jul. 21, 2009

(65) Prior Publication Data

US 2009/0292333 A1 Nov. 26, 2009

Related U.S. Application Data

(63) Continuation of application No. 11/592,095, filed on Nov. 2, 2006, now Pat. No. 7,725,188.

(60) Provisional application No. 60/814,312, filed on Jun. 16, 2006, provisional application No. 60/772,361, filed on Feb. 10, 2006.

(51) Int. Cl.
*A61N 1/00* (2006.01)
(52) U.S. Cl. ...................................................... 607/23
(58) Field of Classification Search .................. 607/9, 607/2–4, 18, 23, 46; 600/500
See application file for complete search history.

(56) References Cited

U.S. PATENT DOCUMENTS

| 3,946,745 | A | 3/1976 | Hsiang-Lai et al. |
| 3,949,743 | A | 4/1976 | Shanbrom |
| 4,305,402 | A | 12/1981 | Katims |
| 4,351,330 | A | 9/1982 | Scarberry |
| 4,503,863 | A | 3/1985 | Katims |
| 4,649,935 | A | 3/1987 | Charmillot et al. |
| 4,765,322 | A | 8/1988 | Charmillot et al. |
| 4,904,472 | A | 2/1990 | Belardinelli et al. |
| 4,945,910 | A | 8/1990 | Budyko et al. |
| 4,989,604 | A | 2/1991 | Fang |
| 5,054,486 | A | 10/1991 | Yamada |

(Continued)

FOREIGN PATENT DOCUMENTS

WO    WO 01/89526 A1    11/2001

(Continued)

OTHER PUBLICATIONS

International Search Report and Written Opinion of International Application PCT/US06/42828.

(Continued)

*Primary Examiner*—George Manuel
*Assistant Examiner*—Robert N Wieland
(74) *Attorney, Agent, or Firm*—John T. Raffle

(57) ABSTRACT

Methods and devices for treating hypotension, such as in cases of shock, including septic shock and anaphylactic shock, wherein the treatment includes providing an electrical impulse to a selected region of the vagus nerve of a patient suffering from hypotension to block and/or modulate nerve signals that regulate blood pressure.

33 Claims, 13 Drawing Sheets

U.S. PATENT DOCUMENTS

| | | |
|---|---|---|
| 5,107,835 A | 4/1992 | Thomas |
| 5,109,846 A | 5/1992 | Thomas |
| 5,123,413 A | 6/1992 | Hasegawa et al. |
| 5,135,480 A | 8/1992 | Bannon et al. |
| 5,152,286 A | 10/1992 | Sitko et al. |
| 5,405,362 A | 4/1995 | Kramer et al. |
| 5,405,366 A | 4/1995 | Fox et al. |
| 5,454,840 A | 10/1995 | Krakovsky et al. |
| 5,540,730 A | 7/1996 | Terry, Jr. et al. |
| 5,620,463 A | 4/1997 | Drolet |
| 5,658,322 A | 8/1997 | Fleming |
| 5,690,692 A | 11/1997 | Fleming |
| 5,707,400 A | 1/1998 | Terry, Jr. et al. |
| 5,814,078 A | 9/1998 | Zhou et al. |
| 5,849,026 A | 12/1998 | Zhou et al. |
| 5,891,182 A | 4/1999 | Fleming |
| 5,911,218 A | 6/1999 | DiMarco |
| 5,931,806 A | 8/1999 | Shimada |
| 5,956,501 A | 9/1999 | Brown |
| 5,972,026 A | 10/1999 | Laufer et al. |
| 5,995,873 A | 11/1999 | Rhodes |
| 6,006,134 A | 12/1999 | Hill et al. |
| 6,043,273 A | 3/2000 | Duhaylongsod |
| 6,060,454 A | 5/2000 | Duhaylongsod |
| 6,083,249 A | 7/2000 | Familoni |
| 6,083,255 A | 7/2000 | Laufer et al. |
| 6,087,394 A | 7/2000 | Duhaylongsod |
| 6,101,412 A | 8/2000 | Duhaylongsod |
| 6,125,301 A | 9/2000 | Capel |
| 6,127,410 A | 10/2000 | Duhaylongsod |
| 6,141,589 A | 10/2000 | Duhaylongsod |
| 6,198,970 B1 | 3/2001 | Freed et al. |
| 6,200,333 B1 | 3/2001 | Laufer |
| 6,203,562 B1 | 3/2001 | Ohkubo |
| 6,212,432 B1 | 4/2001 | Matsuura |
| 6,230,052 B1 | 5/2001 | Wolff et al. |
| 6,258,087 B1 | 7/2001 | Edwards et al. |
| 6,273,886 B1 | 8/2001 | Edwards et al. |
| 6,273,907 B1 | 8/2001 | Laufer |
| 6,283,988 B1 | 9/2001 | Laufer et al. |
| 6,283,989 B1 | 9/2001 | Laufer et al. |
| 6,299,633 B1 | 10/2001 | Laufer |
| 6,325,798 B1 | 12/2001 | Edwards et al. |
| 6,327,503 B1 | 12/2001 | Familoni |
| 6,341,236 B1 | 1/2002 | Osorio et al. |
| 6,342,221 B1 | 1/2002 | Thorpe et al. |
| 6,347,247 B1 | 2/2002 | Dev |
| 6,356,786 B1 | 3/2002 | Rezai et al. |
| 6,356,787 B1 | 3/2002 | Rezai et al. |
| 6,363,937 B1 | 4/2002 | Hovda et al. |
| 6,366,814 B1 | 4/2002 | Boveja et al. |
| 6,402,744 B2 | 6/2002 | Edwards et al. |
| 6,411,852 B1 | 6/2002 | Danek et al. |
| 6,414,018 B1 | 7/2002 | Duhaylongsod |
| 6,423,058 B1 | 7/2002 | Edwards et al. |
| 6,424,864 B1 | 7/2002 | Matsuura |
| 6,438,423 B1 | 8/2002 | Rezai et al. |
| 6,440,128 B1 | 8/2002 | Edwards et al. |
| 6,464,697 B1 | 10/2002 | Edwards et al. |
| 6,485,416 B1 | 11/2002 | Platt et al. |
| 6,547,776 B1 | 4/2003 | Gaiser et al. |
| 6,549,808 B1 | 4/2003 | Gisel et al. |
| 6,562,034 B2 | 5/2003 | Edwards et al. |
| 6,587,719 B1 | 7/2003 | Barrett et al. |
| 6,609,025 B2 | 8/2003 | Barrett |
| 6,609,030 B1 | 8/2003 | Rezai et al. |
| 6,610,713 B2 | 8/2003 | Tracey |
| 6,612,983 B1 | 9/2003 | Marchal |
| 6,629,951 B2 | 10/2003 | Laufer et al. |
| 6,633,779 B1 | 10/2003 | Schuler et al. |
| 6,656,960 B2 | 12/2003 | Puskas |
| 6,675,047 B1 | 1/2004 | Konoplev et al. |
| 6,676,686 B2 | 1/2004 | Naganuma |
| 6,681,136 B2 | 1/2004 | Schuler et al. |
| 6,711,436 B1 | 3/2004 | Duhaylongsod |
| 6,712,074 B2 | 3/2004 | Edwards et al. |
| 6,738,667 B2 | 5/2004 | Deno et al. |
| 6,752,765 B1 | 6/2004 | Jensen et al. |
| 6,755,849 B1 | 6/2004 | Gowda et al. |
| 6,778,854 B2 | 8/2004 | Puskas |
| 6,811,536 B2 * | 11/2004 | Sun et al. ............... 600/500 |
| 6,819,956 B2 | 11/2004 | DiLorenzo |
| 6,838,429 B2 | 1/2005 | Paslin |
| 6,865,416 B2 | 3/2005 | Dev |
| 6,871,092 B2 | 3/2005 | Piccone |
| 6,871,099 B1 | 3/2005 | Whitehurst et al. |
| 6,872,206 B2 | 3/2005 | Edwards et al. |
| 6,885,888 B2 | 4/2005 | Rezai |
| 6,913,616 B2 | 7/2005 | Hamilton et al. |
| 6,934,583 B2 | 8/2005 | Weinberg et al. |
| 6,937,896 B1 | 8/2005 | Kroll |
| 6,937,903 B2 | 8/2005 | Schuler et al. |
| 6,957,106 B2 | 10/2005 | Schuler et al. |
| 6,961,622 B2 | 11/2005 | Gilbert |
| 6,970,742 B2 | 11/2005 | Mann et al. |
| 6,973,347 B1 | 12/2005 | Ben-Haim |
| 6,974,224 B2 | 12/2005 | Thomas-Benedict |
| 7,031,745 B2 | 4/2006 | Shen |
| 7,072,720 B2 | 7/2006 | Puskas |
| 7,092,755 B2 | 8/2006 | Florio |
| 7,123,961 B1 | 10/2006 | Kroll |
| 7,142,910 B2 | 11/2006 | Puskas |
| 7,167,750 B2 | 1/2007 | Knudson |
| 7,203,548 B2 | 4/2007 | Whitehurst |
| 7,225,019 B2 | 5/2007 | Jahns |
| 7,228,167 B2 | 6/2007 | Kara |
| 7,292,890 B2 | 11/2007 | Whitehurst |
| 7,310,552 B2 | 12/2007 | Puskas |
| 7,363,076 B2 * | 4/2008 | Yun et al. ............... 607/3 |
| 7,493,161 B2 * | 2/2009 | Libbus et al. ............ 607/4 |
| 2002/0002387 A1 | 1/2002 | Naganuma |
| 2002/0010495 A1 | 1/2002 | Freed et al. |
| 2002/0016344 A1 | 2/2002 | Tracey |
| 2002/0016615 A1 | 2/2002 | Dev |
| 2002/0072738 A1 | 6/2002 | Edwards et al. |
| 2002/0087192 A1 | 7/2002 | Barrett |
| 2002/0091379 A1 | 7/2002 | Danek et al. |
| 2002/0107515 A1 | 8/2002 | Edwards et al. |
| 2002/0111386 A1 | 8/2002 | Sekins et al. |
| 2002/0116030 A1 | 8/2002 | Rezai |
| 2002/0143373 A1 | 10/2002 | Courtnage et al. |
| 2002/0151888 A1 | 10/2002 | Edwards et al. |
| 2002/0183682 A1 | 12/2002 | Darvish et al. |
| 2002/0198570 A1 | 12/2002 | Puskas |
| 2002/0198574 A1 | 12/2002 | Gumpert |
| 2002/0198575 A1 | 12/2002 | Sullivan |
| 2003/0023287 A1 | 1/2003 | Edwards et al. |
| 2003/0074039 A1 | 4/2003 | Puskas |
| 2003/0093128 A1 | 5/2003 | Freed et al. |
| 2003/0144572 A1 | 7/2003 | Oschman et al. |
| 2003/0181949 A1 | 9/2003 | Whale |
| 2003/0216791 A1 | 11/2003 | Schuler et al. |
| 2003/0216792 A1 | 11/2003 | Levin et al. |
| 2003/0233099 A1 | 12/2003 | Danaek et al. |
| 2004/0010289 A1 | 1/2004 | Biggs et al. |
| 2004/0029849 A1 | 2/2004 | Schatzberg et al. |
| 2004/0030368 A1 | 2/2004 | Kemeny et al. |
| 2004/0044390 A1 | 3/2004 | Szeles |
| 2004/0059383 A1 | 3/2004 | Puskas |
| 2004/0073278 A1 | 4/2004 | Pachys |
| 2004/0088030 A1 | 5/2004 | Jung, Jr. |
| 2004/0088036 A1 | 5/2004 | Gilbert |
| 2004/0106954 A1 | 6/2004 | Whitehurst et al. |
| 2004/0116981 A1 | 6/2004 | Mazar |

| | | |
|---|---|---|
| 2004/0122488 A1 | 6/2004 | Mazar et al. |
| 2004/0122489 A1 | 6/2004 | Mazar et al. |
| 2004/0127942 A1 | 7/2004 | Yomtov et al. |
| 2004/0127958 A1 | 7/2004 | Mazar et al. |
| 2004/0147969 A1 | 7/2004 | Mann et al. |
| 2004/0147988 A1 | 7/2004 | Stephens |
| 2004/0162597 A1 | 8/2004 | Hamilton et al. |
| 2004/0167580 A1 | 8/2004 | Mann et al. |
| 2004/0172075 A1 | 9/2004 | Shafer et al. |
| 2004/0172080 A1 | 9/2004 | Stadler et al. |
| 2004/0172084 A1 | 9/2004 | Knudson et al. |
| 2004/0176803 A1 | 9/2004 | Whelan et al. |
| 2004/0176805 A1 | 9/2004 | Whelan et al. |
| 2004/0204747 A1 | 10/2004 | Kemeny et al. |
| 2004/0215289 A1 | 10/2004 | Fukui |
| 2004/0220621 A1 | 11/2004 | Zhou et al. |
| 2004/0230251 A1 | 11/2004 | Schuler et al. |
| 2004/0230252 A1 | 11/2004 | Kullok et al. |
| 2004/0249416 A1 | 12/2004 | Yun et al. |
| 2005/0004609 A1 | 1/2005 | Stahmann et al. |
| 2005/0004631 A1 | 1/2005 | Benedict |
| 2005/0010263 A1 | 1/2005 | Schauerte |
| 2005/0010270 A1 | 1/2005 | Laufer |
| 2005/0015117 A1 | 1/2005 | Gerber |
| 2005/0021092 A1 | 1/2005 | Yun et al. |
| 2005/0059153 A1 | 3/2005 | George et al. |
| 2005/0065553 A1 | 3/2005 | Ezra et al. |
| 2005/0065562 A1 | 3/2005 | Rezai |
| 2005/0065567 A1 | 3/2005 | Lee et al. |
| 2005/0065573 A1 | 3/2005 | Rezai |
| 2005/0065574 A1 | 3/2005 | Rezai |
| 2005/0075701 A1 | 4/2005 | Shafer |
| 2005/0075702 A1 | 4/2005 | Shafer |
| 2005/0076909 A1 | 4/2005 | Stahmann et al. |
| 2005/0080461 A1 | 4/2005 | Stahmann et al. |
| 2005/0090722 A1 | 4/2005 | Perez |
| 2005/0107829 A1 | 5/2005 | Edwards et al. |
| 2005/0125044 A1 | 6/2005 | Tracey |
| 2005/0143788 A1 | 6/2005 | Yun et al. |
| 2005/0149146 A1 | 7/2005 | Boveja et al. |
| 2005/0153885 A1 | 7/2005 | Yun et al. |
| 2005/0159736 A9 | 7/2005 | Danek et al. |
| 2005/0165456 A1 | 7/2005 | Mann et al. |
| 2005/0171575 A1 | 8/2005 | Dev |
| 2005/0177192 A1 | 8/2005 | Rezai et al. |
| 2005/0182288 A1 | 8/2005 | Zabara |
| 2005/0182463 A1 | 8/2005 | Hunter |
| 2005/0187579 A1 | 8/2005 | Danek et al. |
| 2005/0187581 A1 | 8/2005 | Hara |
| 2005/0216062 A1 | 9/2005 | Herbst |
| 2005/0222628 A1 | 10/2005 | Krakousky |
| 2005/0222635 A1 | 10/2005 | Krakovsky |
| 2005/0222651 A1 | 10/2005 | Jung, Jr. |
| 2005/0228054 A1 | 10/2005 | Tatton |
| 2005/0228459 A1 | 10/2005 | Levin et al. |
| 2005/0228460 A1 | 10/2005 | Levin et al. |
| 2005/0234523 A1 | 10/2005 | Levin et al. |
| 2005/0238693 A1 | 10/2005 | Whyte |
| 2005/0240241 A1 | 10/2005 | Yun et al. |
| 2005/0245992 A1 | 11/2005 | Persen et al. |
| 2005/0251213 A1 | 11/2005 | Freeman |
| 2005/0256028 A1 | 11/2005 | Yun et al. |
| 2005/0261747 A1 | 11/2005 | Schuler et al. |
| 2005/0267536 A1 | 12/2005 | Freeman et al. |
| 2005/0277993 A1 | 12/2005 | Mower |
| 2005/0283197 A1 | 12/2005 | Daum et al. |
| 2006/0095079 A1 | 5/2006 | Gerber |
| 2006/0129216 A1 | 6/2006 | Hastings |
| 2006/0135998 A1* | 6/2006 | Libbus et al. ............ 607/2 |
| 2006/0167498 A1 | 7/2006 | DiLorenzo |
| 2006/0178703 A1 | 8/2006 | Huston |
| 2006/0200219 A1 | 9/2006 | Thorp |
| 2006/0229677 A1 | 10/2006 | Moffitt |
| 2006/0259107 A1 | 11/2006 | Caparso |
| 2006/0282145 A1 | 12/2006 | Caparso |
| 2006/0287679 A1 | 12/2006 | Stone |
| 2007/0027483 A1 | 2/2007 | Maschino |
| 2007/0027496 A1 | 2/2007 | Parnis et al. |
| 2007/0060954 A1 | 3/2007 | Cameron |
| 2007/0093870 A1 | 4/2007 | Maschino |
| 2007/0106337 A1 | 5/2007 | Errico |
| 2007/0106338 A1 | 5/2007 | Errico |
| 2007/0106339 A1 | 5/2007 | Errico et al. |
| 2007/0135846 A1 | 6/2007 | Knudsosn |
| 2007/0150006 A1 | 6/2007 | Libbus |
| 2007/0156182 A1 | 7/2007 | Castel |
| 2007/0191902 A1 | 8/2007 | Errico et al. |
| 2007/0225768 A1 | 9/2007 | Dobak, III |
| 2007/0239210 A1 | 10/2007 | Libbus |
| 2007/0250119 A1 | 10/2007 | Tyler |
| 2007/0299476 A1 | 12/2007 | Park |
| 2008/0004672 A1 | 1/2008 | Dalal |
| 2008/0183248 A1 | 7/2008 | Rezai et al. |

FOREIGN PATENT DOCUMENTS

WO    WO 2004/078252 A2    9/2004

OTHER PUBLICATIONS

International Preliminary Report on Patentablility for corresponding patent PCT/US2006/042828, dated Aug. 21, 2008.

International Search Report and Written Opinion of the International Searching Authority dated May 20, 2009 of International Application No. PCT/US2009/038081, International filing date Mar. 24, 2009.

International Search Report and Written Opinion of the International Searching Authority dated Jan. 29, 2008 of International Application No. PCT/US06/42752, International filing date Nov. 1, 2006.

International Search Report and Written Opinion of the International Searching Authority dated Mar. 16, 2007 of International Application No. PCT/US2006/042823, International filing date Nov. 2, 2006.

Guarini et al., "Efferent Vagal Fibre Stimulation Blunts Nuclear Factor-kB Activation and Protects Against Hypovolemic Hemorrhagic Shock", *Circulation* 2003 vol. 107 pp. 1189-1194.

Supplemental European Search Report for EP Application No. 06827343, Aug. 21, 2009.

Supplemental European Search Report for EP Application No. 06827386.1, Aug. 21, 2009.

U.S. Appl. No. 60/206,364, Title: Vagus Nerve Stimulation Attenuation of the Systemic Inflammatory Response to Endotoxin, filed May 23, 2000, Inventor: Tracey.

* cited by examiner

ELECTRICAL STIMULATION TREATMENT OF HYPOTENSION

CROSS REFERENCE TO RELATED APPLICATIONS

This application is a continuation application of U.S. patent application Ser. No. 11/592,095 filed Nov. 2, 2006, now U.S. Pat. No. 7,725,188 issued May 25, 2010; which claims the benefit of U.S. provisional patent application nos.: 60/814,312, filed Jun. 16, 2006 and 60/772,361, filed Feb. 10, 2006, the entire disclosures of which are hereby incorporated by reference.

BACKGROUND OF THE INVENTION

The present invention relates to the field of delivery of electrical impulses to bodily tissues for therapeutic purposes, and more specifically to devices and methods for treating conditions associated with hypotension by blocking and/or modulating signals in the vagus nerve, to facilitate stronger heart function and/or affect vasoconstriction.

There are a number of treatments for various infirmities that require the destruction of otherwise healthy tissue in order to affect a beneficial effect. Malfunctioning tissue is identified, and then lesioned or otherwise compromised in order to affect a beneficial outcome, rather than attempting to repair the tissue to its normal functionality. While there are a variety of different techniques and mechanisms that have been designed to focus lesioning directly onto the target nerve tissue, collateral damage is inevitable.

Still other treatments for malfunctioning tissue can be medicinal in nature, in many cases leaving patients to become dependent upon artificially synthesized chemicals. Examples of this are anti-asthma drugs such as albuterol, proton pump inhibitors such as omeprazole (Prilosec), spastic bladder relievers such as Ditropan, and cholesterol reducing drugs like Lipitor and Zocor. In many cases, these medicinal approaches have side effects that are either unknown or quite significant, for example, at least one popular diet pill of the late 1990's was subsequently found to cause heart attacks and strokes.

Unfortunately, the beneficial outcomes of surgery and medicines are, therefore, often realized at the cost of function of other tissues, or risks of side effects.

The use of electrical stimulation for treatment of medical conditions has been well known in the art for nearly two thousand years. It has been recognized that electrical stimulation of the brain and/or the peripheral nervous system and/or direct stimulation of the malfunctioning tissue, which stimulation is generally a wholly reversible and non-destructive treatment, holds significant promise for the treatment of many ailments.

Electrical stimulation of the brain with implanted electrodes has been approved for use in the treatment of various conditions, including pain and movement disorders including essential tremor and Parkinson's disease. The principle behind these approaches involves disruption and modulation of hyperactive neuronal circuit transmission at specific sites in the brain. As compared with the very dangerous lesioning procedures in which the portions of the brain that are behaving pathologically are physically destroyed, electrical stimulation is achieved by implanting electrodes at these sites to, first sense aberrant electrical signals and then to send electrical pulses to locally disrupt the pathological neuronal transmission, driving it back into the normal range of activity. These electrical stimulation procedures, while invasive, are generally conducted with the patient conscious and a participant in the surgery.

Brain stimulation, and deep brain stimulation in particular, is not without some drawbacks. The procedure requires penetrating the skull, and inserting an electrode into the brain matter using a catheter-shaped lead, or the like.

While monitoring the patient's condition (such as tremor activity, etc.), the position of the electrode is adjusted to achieve significant therapeutic potential. Next, adjustments are made to the electrical stimulus signals, such as frequency, periodicity, voltage, current, etc., again to achieve therapeutic results. The electrode is then permanently implanted and wires are directed from the electrode to the site of a surgically implanted pacemaker. The pacemaker provides the electrical stimulus signals to the electrode to maintain the therapeutic effect. While the therapeutic results of deep brain stimulation are promising, there are significant complications that arise from the implantation procedure, including stroke induced by damage to surrounding tissues and the neurovasculature.

One of the most successful modern applications of this basic understanding of the relationship between muscle and nerves is the cardiac pacemaker. Although its roots extend back into the 1800's, it was not until 1950 that the first practical, albeit external and bulky pacemaker was developed. Dr. Rune Elqvist developed the first truly functional, wearable pacemaker in 1957. Shortly thereafter, in 1960, the first fully implanted pacemaker was developed.

Around this time, it was also found that the electrical leads could be connected to the heart through veins, which eliminated the need to open the chest cavity and attach the lead to the heart wall. In 1975 the introduction of the lithium-iodide battery prolonged the battery life of a pacemaker from a few months to more than a decade. The modern pacemaker can treat a variety of different signaling pathologies in the cardiac muscle, and can serve as a defibrillator as well (see U.S. Pat. No. 6,738,667 to Deno, et al., the disclosure of which is incorporated herein by reference).

Another application of electrical stimulation of nerves has been the treatment of radiating pain in the lower extremities by means of stimulation of the sacral nerve roots at the bottom of the spinal cord (see U.S. Pat. No. 6,871,099 to Whitehurst, et al., the disclosure of which is incorporated herein by reference).

A further application is disclosed in U.S. Pat. No. 6,957,106 ("'106") to Schuler, et al., titled, "Implantable method to regulate blood pressure by means of coded nerve signals," which is incorporated in its entirety by reference. The '106 patent states that, "the electrical action for regulating cardiovascular blood pressure emerges from the medullopontine area via the vagus nerve bundle." Affecting the electrical action of the vagus nerve bundle therefore may affect regulation of blood pressure, making the vagus nerve a further subject of electrical stimulation study.

Most of the life support control of the human or animal body is via the vagus (or tenth cranial) nerve that exits from the medulla oblongata. This nerve is actually a long bundle of afferent and efferent neurons that travels over the internal body to most organs. The vagus nerve emerges from each side of the medulla and travels different routes to the same target organs. Paralysis or severing the two vagus nerves at the level of the medulla or neck is rapidly fatal.

Blood pressure is the pressure exerted by the blood on the walls of the blood vessels. Unless indicated otherwise, blood pressure refers to systemic arterial blood pressure, i.e., the pressure in the large arteries delivering blood to body parts other than the lungs, such as the brachial artery (in the arm).

The pressure of the blood in other vessels is lower than the arterial pressure. Blood pressure values are universally stated in millimetres of mercury (mm Hg), and are always given relative to atmospheric pressure. For example, the absolute pressure of the blood in an artery with mean arterial pressure stated as 100 mm Hg, on a day with atmospheric pressure of 760 mm Hg, is 860 mm Hg.

The systolic pressure is defined as the peak pressure in the arteries during the cardiac cycle; the diastolic pressure is the lowest pressure (at the resting phase of the cardiac cycle). The mean arterial pressure and pulse pressure are other important quantities. Typical values for a resting, healthy adult are approximately 120 mm Hg systolic and 80 mm Hg diastolic (written as 120/80 mm Hg), with large individual variations. These measures of blood pressure are not static, but undergo natural variations from one heartbeat to another or throughout the day (in a circadian rhythm); they also change in response to stress, nutritional factors, drugs, or disease.

An instance of the connection between the vagus nerve and blood pressure regulation may be found in U.S. Pat. No. 5,707,400 ("'400"), to Terry, et al., titled, "Treating refractory hypertension by nerve stimulation," which is incorporated in its entirety by reference. Hypertension (higher than normal blood pressure) and its converse, hypotension (lower than normal blood pressure), largely comprise the two sides of the coin that represents the problems relating to blood pressure. Issuing relating to hypotension, its causes and effects, are discussed also in U.S. Patent Application Number 20050283197 A1, to Daum, et al., titled, "Systems and methods for hypotension," which is incorporated in its entirety by reference.

Blood pressure exceeding normal values is called arterial hypertension. It itself is only rarely an acute problem, with the seldom exception of hypertensive crisis, such as severe hypertension with acute impairment of an organ system (especially the central nervous system, cardiovascular system and/or the renal system) and the possibility of irreversible organ-damage. However, because of its long-term indirect effects (and also as an indicator of other problems) it is a serious worry to physicians diagnosing it. Persistent hypertension is one of the risk factors for strokes, heart attacks, heart failure, arterial aneurysms, and is the second leading cause of chronic renal failure after diabetes mellitus.

All level of blood pressure puts mechanical stress on the arterial walls. Higher pressures increase heart workload and progression of unhealthy tissue growth (atheroma) that develops within the walls of arteries. The higher the pressure, the more stress that is present and the more atheroma tend to progress and the heart muscle tends to thicken, enlarge and become weaker over time.

Blood pressure that is too low is known as hypotension. Low blood pressure may be a sign of severe disease and requires more urgent medical attention. When blood pressure and blood flow is very low, the perfusion of the brain may be critically decreased (i.e., the blood supply is not sufficient), causing lightheadedness, dizziness, weakness and fainting.

Sometimes the blood pressure drops significantly when a patient stands up from sitting. This is known as orthostatic hypotension; gravity reduces the rate of blood return from the body veins below the heart back to the heart, thus reducing stroke volume and cardiac output. When people are healthy, they quickly constrict the veins below the heart and increase their heart rate to minimize and compensate for the gravity effect. This is done at a subconscious level via the autonomic nervous system. The system usually requires a few seconds to fully adjust and if the compensations are too slow or inadequate, the individual will suffer reduced blood flow to the brain, dizziness and potential blackout. Increases in G-loading, such as routinely experienced by supersonic jet pilots "pulling Gs", greatly increases this effect. Repositioning the body perpendicular to gravity largely eliminates the problem.

Hypotension often accompanies and complicates many other systemic health problems, such as anaphylaxis and sepsis, leading to anaphylactic shock and septic shock, making it more difficult to address the underlying health problem. For example, U.S. Patent Application Number 20050065553, Ben Ezra, et al., titled, "Applications of vagal stimulation," which is incorporated in its entirety by reference, proposes to a method to treat a patient's sepsis by applying an appropriately configured current to the vagus nerve. However, when accompanied with refractory arterial hypotension, sepsis becomes septic shock.

Septic shock is a serious medical condition causing such effects as multiple organ failure and death in response to infection and sepsis. Its most common victims are children and the elderly, as their immune systems cannot cope with the infection as well as those of full-grown adults, as well as immunocompromised individuals. The mortality rate from septic shock is approximately 50%. Other various shock conditions include: systemic inflammatory response syndrome, toxic shock syndrome, adrenal insufficiency, and anaphylaxis.

A subclass of distributive shock, shock refers specifically to decreased tissue perfusion resulting in end-organ dysfunction. Cytokines TNFα, IL-1β, IL-6 released in a large scale inflammatory response may result in massive vasodilation, increased capillary permeability, decreased systemic vascular resistance, and hypotension. Hypotension reduces tissue perfusion pressure, and thus tissue hypoxia ensues. Finally, in an attempt to offset decreased blood pressure, ventricular dilatation and myocardial dysfunction will occur.

Myocardial dysfunction involves a decrease in overall myocardial performance. The determinants of myocardial performance are heart rate, preload, afterload, and contractility.

Heart rate is a term used to describe the frequency of the cardiac cycle, usually in number of number of contractions of the heart (heart beats) per minute. The heart contains two natural cardiac pacemakers that spontaneously cause the heart to beat. These can be controlled by the autonomic nervous system and circulating adrenaline.

The body can increase the heart rate in response to a wide variety of conditions in order to increase the cardiac output (the amount of blood ejected by the heart per unit time). Exercise, environmental stressors or psychological stress can cause the heart rate to increase above the resting rate. The pulse is the most straightforward way of measuring the heart rate, but it can be deceptive when some strokes do not lead to much cardiac output. In these cases (as happens in some arrhythmias), the heart rate may be considerably higher than the pulse.

Preload is theoretically most accurately described as the initial stretching of cardiac myocytes prior to contraction. Preload is the volume of blood present in a ventricle of the heart, after passive filling and atrial contraction. Preload is affected by venous blood pressure and the rate of venous return. These are affected by venous tone and volume of circulating blood.

Afterload is the tension produced by a chamber of the heart in order to contract. Afterload can also be described as the pressure that the chamber of the heart has to generate in order to eject blood out of the chamber. In the case of the left ventricle, the afterload is a consequence of the blood pressure, since the pressure in the ventricle must be greater than the blood pressure in order to open the aortic valve. For instance, hypertension (increased blood pressure) increases the left ventricular afterload because the left ventricle has to work harder to eject blood into the aorta. This is because the aortic valve won't open until the pressure generated in the left ventricle is higher than the elevated blood pressure.

Contractility is the intrinsic ability of a cardiac muscle fiber to contract at any given fiber length. If myocardial performance changes while preload, afterload and heart rate are all constant, then the change in performance must be due to the change in contractility. Chemicals that affect contractility are called inotropic agents. For example drugs such as catecholamines (norepinephrine and epinephrine) that enhance contractility are considered to have a positive inotropic effect. All factors that cause an increase in contractility work by causing an increase in intracellular calcium concentration [Ca++] during contraction.

The concept of contractility was necessary to explain why some interventions (e.g. an adrenaline infusion) could cause an increase in myocardial performance even if, as could be shown in experiments, the preload, afterload and heart rate were all held constant. Experimental work controlling the other factors was necessary because a change in contractility is generally not an isolated effect. For example, an increase in sympathetic stimulation to the heart increases contractility and heart rate. An increase in contractility tends to increase stroke volume and thus a secondary decrease in preload.

Accordingly, there is a need in the art for new products and methods for treating the immediate symptoms of hypotension and shock.

SUMMARY OF THE INVENTION

The present invention involves products and methods of treatment of hypotension utilizing an electrical signal that may be applied to the vagus nerve to temporarily block and/or modulate the signals in the vagus nerve. The present invention also encompasses treatment of pathologies causing hypotension, both chronic and acute hypotension, such as in patients with thyroid pathologies and those suffering from septic shock. This treatment of hypotension may accompany treatment for other conditions, such as bronchial constriction, that also may occur in situations of shock.

In a first embodiment, the present invention contemplates an electrical impulse delivery device that delivers one or more electrical impulses to at least one selected region of the vagus nerve to block and/or modulate signals to the muscle fibers of the heart, facilitating contractility.

In a second embodiment, the present invention contemplates a device that delivers one or more electrical impulses to at least one selected region of the vagus nerve to block and/or modulate signals to the fibers surrounding the cardiac tissue, facilitating an increase in heart function, thereby raising blood pressure.

In a third embodiment, the present invention contemplates a device that delivers at least one electrical impulse to at least one selected region of the vagus nerve to block and/or modulate signals to both the fibers surrounding the cardiac tissue, facilitating an increase in heart function, thereby raising blood pressure, and the muscle fibers surrounding the bronchi, facilitating opening of airways.

In yet another embodiment, methods in accordance with the present invention contemplate delivery of one or more electrical impulses to at least one selected region of the vagus nerve to block and/or modulate signals to the muscle fibers of the heart, facilitating contractility.

In another embodiment a method is provided of delivering one or more electrical impulses to at least one selected region of the vagus nerve to block and/or modulate signals to the fibers surrounding the cardiac tissue, facilitating an increase in heart function, thereby raising blood pressure.

In yet another embodiment, the present invention contemplates a method of delivering at least one electrical impulse to at least one selected region of the vagus nerve to block and/or modulate signals to both the fibers surrounding the cardiac tissue, facilitating an increase in heart function, thereby raising blood pressure, and the muscle fibers surrounding the bronchi, facilitating opening of airways.

It shall be understood that the activation of such impulses may be directed manually by a patient suffering from hypotension, such as during shock, depending on the embodiment.

Although the invention is not limited by any theory of operation, in one or more embodiments of the present invention, it is believed that the impulses may be applied in such a manner that the myocardium is relaxed to reduce the baseline level of tonic contraction, vasoconstriction occurs to increase blood pressure, and/or in cases of some shock, the smooth muscle lining the bronchial passages is relaxed to relieve the spasms that occur, such as during anaphylactic shock. The impulses may be applied by positioning leads on the nerves that control cardiac activity, and bronchial activity respectively, such as the superior and inferior cardiac branches, and the anterior and posterior bronchial branches, of the right and left branches of the vagus nerve, which join with fibers from the sympathetic nerve chain to form the anterior and posterior coronary and pulmonary plexuses. Leads may be positioned above both the cardiac and pulmonary branches of the vagus nerve to include a block and/or modulation of both organs. It shall also be understood that leadless impulses as shown in the art may also be utilized for applying impulses to the target regions.

The mechanisms by which the appropriate impulse is applied to the selected region of the vagus nerve can include positioning the distal ends of an electrical lead or leads in the vicinity of the nervous tissue controlling the myocardium, the vessels to/from the heart (to affect vasodilation and/or vasoconstriction), and possibly pulmonary muscles, which leads are coupled to an implantable or external electrical impulse generating device. The electric field generated at the distal tip of the lead creates a field of effect that permeates the target nerve fibers and causes the blocking and/or modulating of signals to the subject muscles.

The application of electrical impulses, either to the vagus nerve or the fibers branching off the vagus nerve to the cardiac muscles (and optionally the bronchial muscles for increasing pulmonary function) to modulate the parasympathetic tone in order to relax the myocardium, effect vasodilation/vasoconstriction, and optionally the bronchial muscle, is more completely described in the following detailed description of the invention, with reference to the drawings provided herewith, and in claims appended hereto.

Other aspects, features, advantages, etc. will become apparent to one skilled in the art when the description of the invention herein is taken in conjunction with the accompanying drawings.

BRIEF DESCRIPTION OF THE DRAWINGS

For the purposes of illustrating the various aspects of the invention, there are shown in the drawings forms that are presently preferred, it being understood, however, that the invention is not limited by or to the precise data, methodologies, arrangements and instrumentalities shown, but rather only by the claims of an issued utility application.

DETAILED DESCRIPTION OF THE PREFERRED EMBODIMENT

It shall be understood that the embodiments disclosed herein are representative of preferred aspects of the invention and are so provided as examples of the invention. The scope of the invention, however, shall not be limited to the disclosures provided herein, nor by the provisional claims appended hereto.

It has been observed in the literature that the nervous system maintains a balance of the signals carried by the sympathetic and parasympathetic nerves. The vagus nerve, as a source of a signal to constrict cardiac muscle, is thought to provide a baseline level of tonicity in the cardiac muscles, in order to prevent the tissue from expanding too much, and thus is considered responsible for depressing blood pressure to prevent heart exhaustion and dangerous hypertension during extreme exertion.

Specifically, one or more embodiments of the present invention contemplate that the signals carried by the vagus (parasympathetic) nerve to cause a slowing of the heart, possibly in combination with a constriction of the smooth muscle surrounding the bronchial passages. The sympathetic nerve fibers carry the opposing signals that tend to speed up the heart rate, as well as open the bronchial passages. It should be recognized that the signals of the vagus nerve mediate a response similar to that of histamine, while the sympathetic signals generate an effect similar to epinephrine. Given the postulated balance between the parasympathetic and sympathetic signals, removing the parasympathetic signal should create an imbalance emphasizing the sympathetic signal. Along these lines, scientific literature also indicates that severing the vagus nerve in dogs will raise the animals' heart rates, as well as open the bronchial passages, much the same way that epinephrine does.

Figure 1:
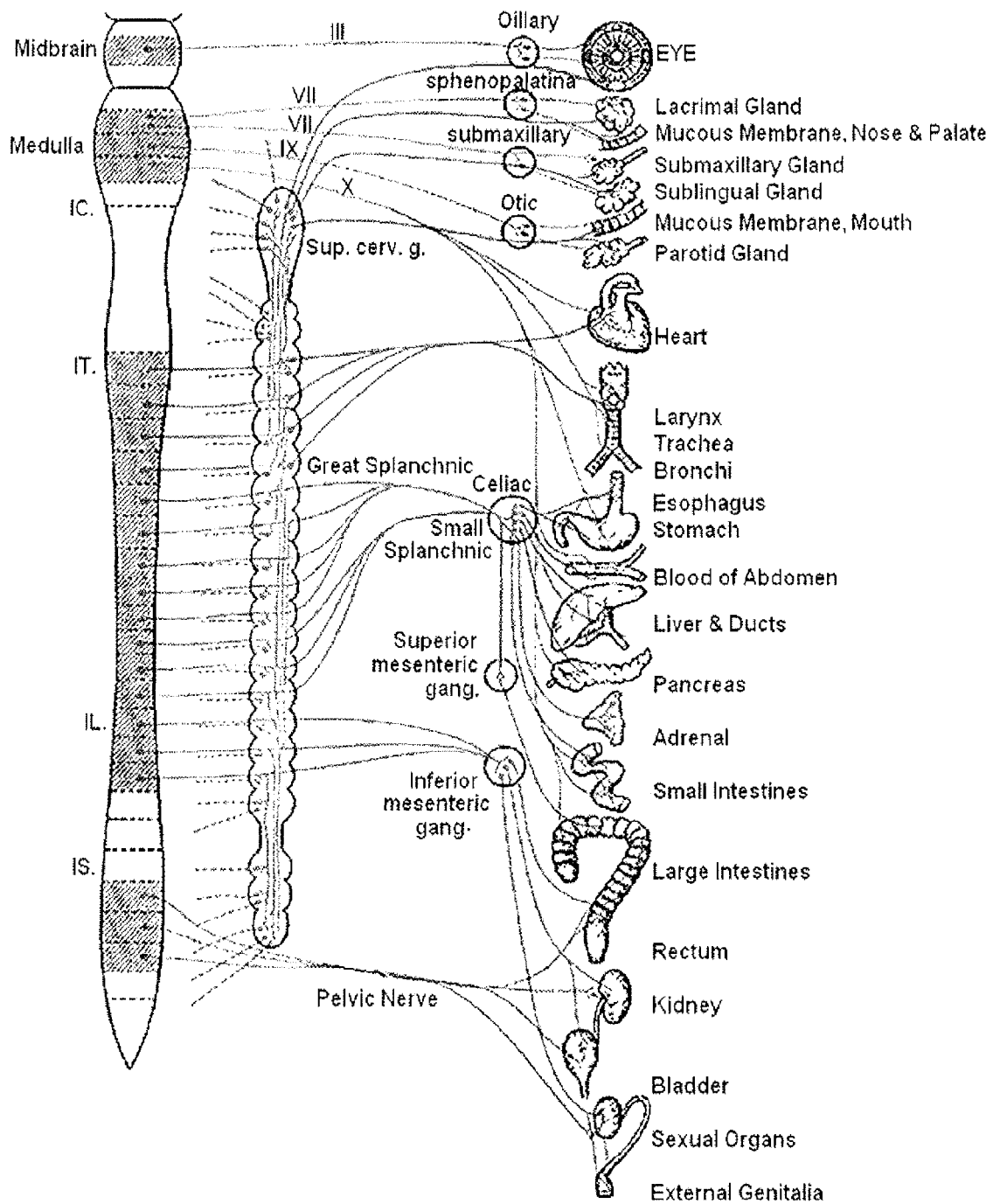
FIG. 1 is a diagrammatic view of the sympathetic and parasympathetic nerve systems.
Figure 2:
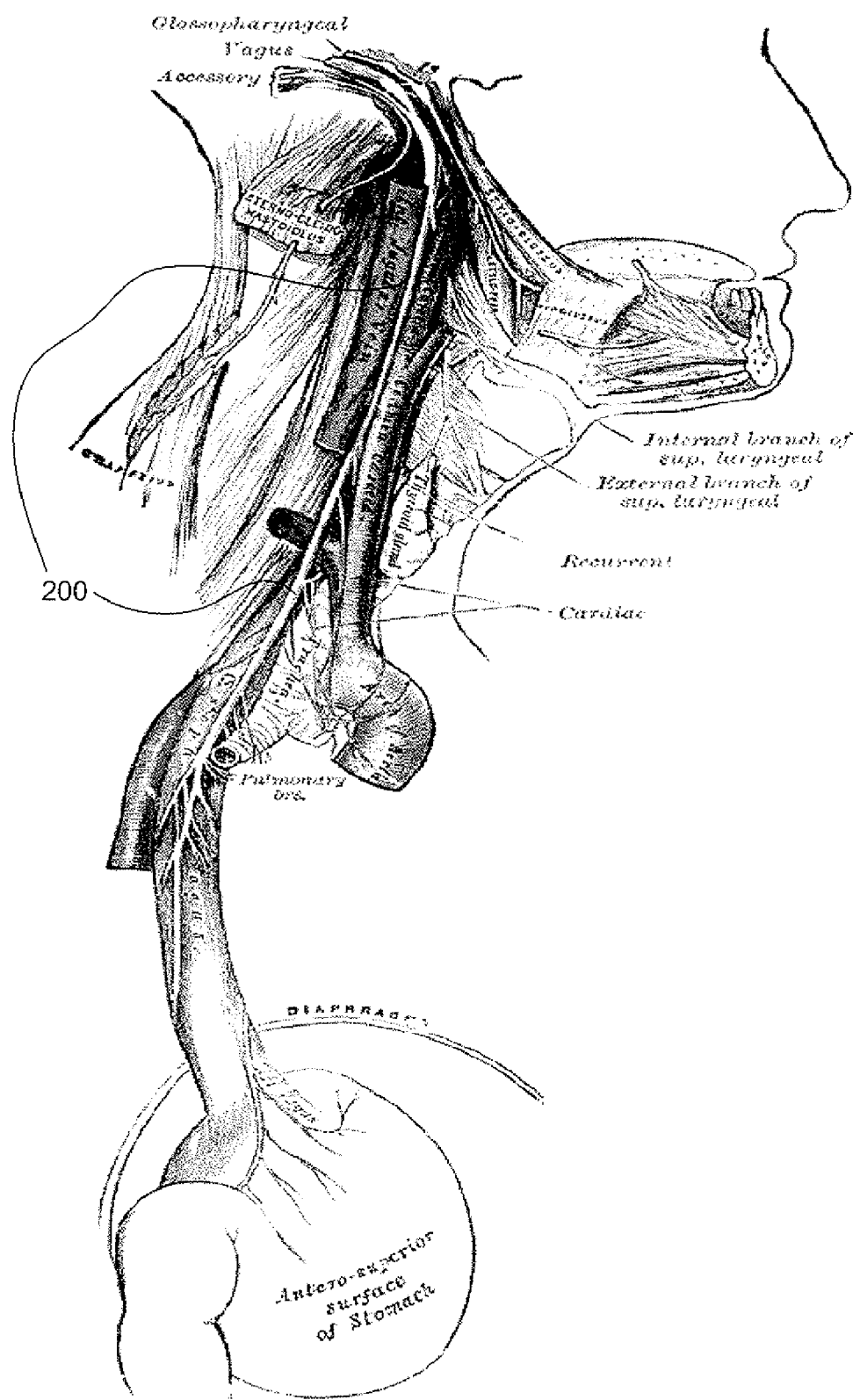
FIG. 2 is a cross-sectional anatomical illustration of selected portions of a neck, thoracic and abdominal region.

Now referring to FIGS. 1 and 2, the vagus nerve is shown in more detail. The vagus nerve is composed of motor and sensory fibers. The vagus nerve leaves the cranium and is contained in the same sheath of dura matter with the accessory nerve. The vagus nerve passes down the neck within the carotid sheath to the root of the neck. Parasympathetic innervation of the heart is mediated by the vagus nerve. The branches of distribution of the vagus nerve include, among others, the superior cardiac, the inferior cardiac, the anterior bronchial and the posterior bronchial branches.

On the right side, the vagus nerve descends by the trachea to the back of the root of the lung, where it spreads out in the inferior cardiac branch and the posterior pulmonary plexus. The right vagus innervates the Sinoatrial node. Parasympathetic hyperstimulation predisposes those affected to bradyarrhythmias. On the left side, the vagus nerve enters the thorax, crosses the left side of the arch of the aorta, forming the superior cardiac branch, and descends behind the root of the left lung, forming the posterior pulmonary plexus. The left vagus when hyperstimulated predisposes the heart to Atrio-ventricular (AV) blocks.

In mammals, two vagal components have evolved in the brainstem to regulate peripheral parasympathetic functions. The dorsal vagal complex (DVC), consisting of the dorsal motor nucleus (DMNX) and its connections, controls parasympathetic function below the level of the diaphragm, while the ventral vagal complex (VVC), comprised of nucleus ambiguous and nucleus retrofacial, controls functions above the diaphragm in organs such as the heart, thymus and lungs, as well as other glands and tissues of the neck and upper chest, and specialized muscles such as those of the esophageal complex.

The parasympathetic portion of the vagus innervates ganglionic neurons which are located in or adjacent to each target organ. The VVC appears only in mammals and is associated with positive as well as negative regulation of heart rate, bronchial constriction, vocalization and contraction of the facial muscles in relation to emotional states. Generally speaking, this portion of the vagus nerve regulates parasympathetic tone. Muscle tone (also known as residual muscle tension) is the continuous and passive partial contraction of the muscles. The VVC inhibition is released (turned off) in states of alertness. This in turn causes cardiac vagal tone to decrease and heart function to increase, and airways to open, to support responses to environmental challenges.

The parasympathetic tone is balanced in part by sympathetic innervation, which generally speaking supplies signals tending to expand the myocardium (and/or effect vasoconstriction), and/or to relax the bronchial muscles, so that over-contraction and over-constriction, respectively, do not occur. Overall, myocardium tone, vasodilation, vasoconstriction, and/or airway smooth muscle tone are dependent on several factors, including parasympathetic input, inhibitory influence of circulating epinephrine, NANC inhibitory nerves and sympathetic innervation of the parasympathetic ganglia. Stimulation of the vagus nerve (up-regulation of tone), such as may occur in shock, results in a heart rate decrease and airway constriction. In this context, up-regulation is the process by which the specific effect is increased, whereas down-regulation involves a decrease of the effect. In general, the pathology of shock appears to be mediated by inflammatory cytokines that overwhelm receptors on the nerve cells and cause the cells to massively up-regulate the parasympathetic tone. On a cellular level, up-regulation is the process by which a cell increases the number of receptors to a given hormone or neurotransmitter to improve its sensitivity to this molecule. A decrease of receptors is called down-regulation.

For instance, sepsis is mediated by severe infection and may result in a large scale inflammatory response that releases cytokines TNFα, IL-1β, IL-6 mediating massive vasodilation, increased capillary permeability, decreased systemic vascular resistance, and hypotension. By comparison, anaphylaxis appears to be mediated predominantly by the hypersensitivity to an allergen causing the massive overproduction of cholinergic receptor activating cytokines that overdrive the otherwise normally operating vagus nerve to signal massive constriction of the airways. Drugs such as epinephrine drive heart rate up while also relaxing the bronchial muscles, effecting temporary relief of symptoms from these conditions. As mentioned above, experience has shown that severing the vagus nerve (an extreme version of reducing the parasympathetic tone) has an effect similar to that of epinephrine and adrenaline on heart rate and bronchial diameter in that the heart begins to race (tachycardia) and the bronchial passageways dilate. However, simply driving up the heart rate may not result in the desired increase in blood pressure, due to the other factors, discussed above, that affect blood pressure.

In accordance with at least one aspect of the present invention, the delivery, in a patient suffering from shock, of an electrical impulse sufficient to block and/or modulate transmission of signals in the vagus nerve will result in raising the heart function, and thus the blood pressure, and depending on the placement of the impulse, relaxation of the bronchi smooth muscle, dilating airways. Preferably, an increase in blood pressure without an increase in heart rate will result.

In accordance with at least one aspect of the present invention, blocking and/or modulating the signal in the vagus nerve to reduce parasympathetic tone provides an immediate emergency response, much like a defibrillator, in situations of shock, providing an immediate increase of heart function. Moreover, the teachings of the present invention permit an immediate heart function increase to enable subsequent life saving measures that otherwise would be ineffective or impossible due to other physiological effects. Treatment in accordance with the present invention provides increased heart function, and optionally bronchodilation, for a long enough period of time so that administered medication such as epinephrine has time to take effect before the patient suffers hypoxia.

The methods described herein of applying an electrical impulse to a selected region of the vagus nerve may further be refined such that the at least one region may comprise at least one nerve fiber emanating from the patient's tenth cranial nerve (the vagus nerve), and in particular, at least one of the superior cardiac branches thereof, or alternatively at least one of the inferior cardiac branches thereof.

The cardiac plexus is situated at the base of the heart, and is divided into a superficial part, which lies in the concavity of the aortic arch, and a deep part, between the aortic arch and the trachea. The two parts are, however, closely connected.

The superficial part of the cardiac plexus lies beneath the arch of the aorta, in front of the right pulmonary artery. It is formed by the superior cardiac branch of the left sympathetic nerve and the lower superior cervical cardiac branch of the left vagus. The superficial part of the cardiac plexus gives branches (a) to the deep part of the plexus; (b) to the anterior coronary plexus; and (c) to the left anterior pulmonary plexus.

The deep part of the cardiac plexus is situated in front of the bifurcation of the trachea, above the point of division of the pulmonary artery, and behind the aortic arch. It is formed by the cardiac nerves derived from the cervical ganglia of the sympathetic, and the cardiac branches of the vagus and recurrent nerves. The only cardiac nerves which do not enter into the formation of the deep part of the cardiac plexus are the superior cardiac nerve of the left sympathetic nerve, and the lower of the two superior cervical cardiac branches from the left vagus, which pass to the superficial part of the plexus.

As necessary, the impulse may be directed to a region of the vagus nerve to block and/or modulate both the cardiac and bronchial branches. As recognized by those having skill in the art, this embodiment should be carefully evaluated prior to use in patients known to have preexisting cardiac issues.

Figure 3:
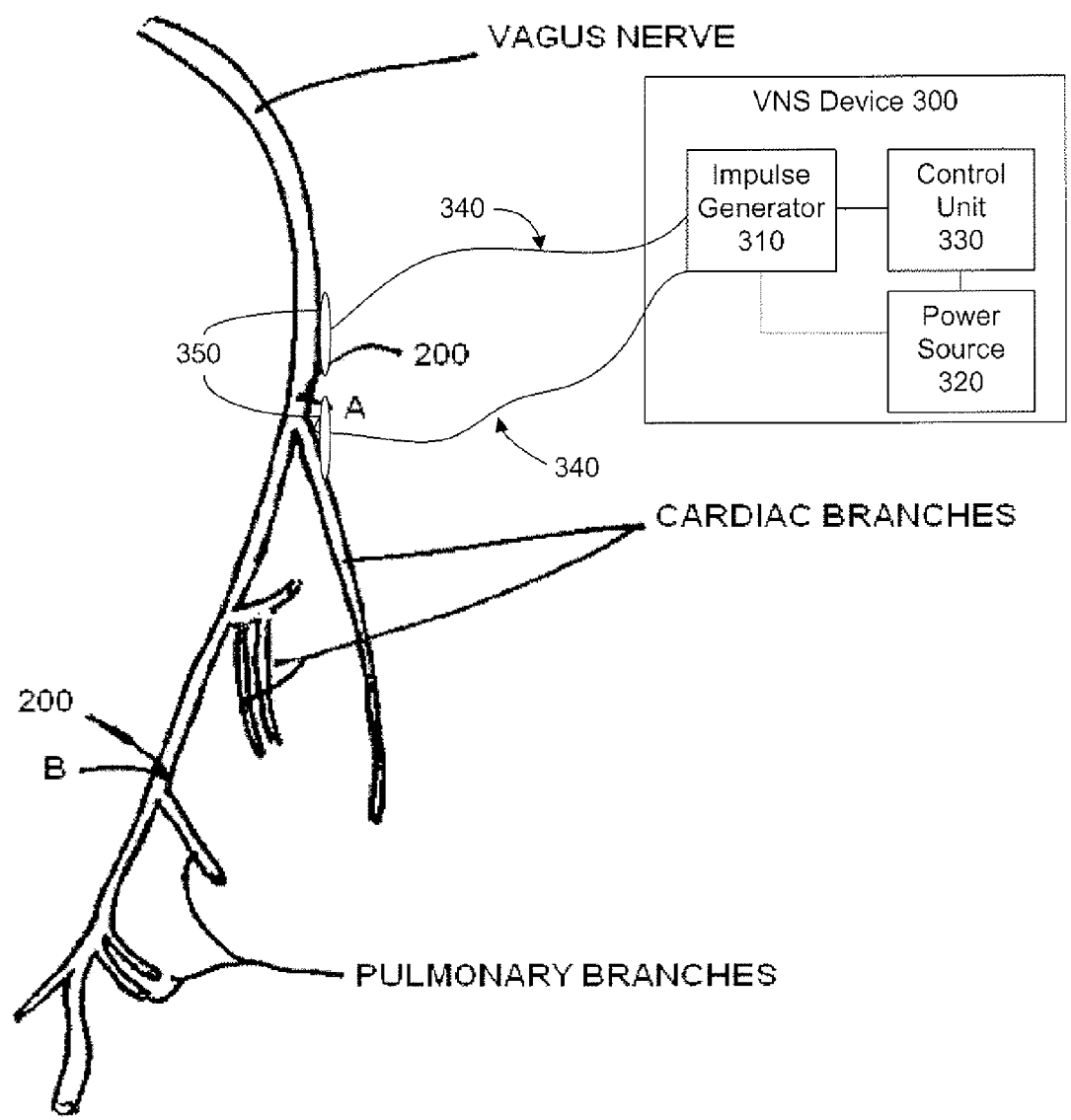
FIG. 3 illustrates a simplified view of the vagus nerve shown in FIGS. 1 and 2.

Further reference is now made to FIG. 3, which illustrates a simplified view of the vagus nerve shown in FIG. 2 and cardiac and pulmonary branches thereof. Also shown is a vagus nerve stimulation (VNS) device 300 for stimulation of the vagus nerve. VNS device 300 is intended for the treatment of hypotension, and optionally bronchial constriction, associated, for example, with shock.

VNS device 300 may include an electrical impulse generator 310; a power source 320 coupled to the electrical impulse generator 310; a control unit 330 in communication with the electrical impulse generator 310 and coupled to the power source 320; and electrodes 340 coupled to the electrical impulse generator 310 for attachment via leads 350 to one or more selected regions 200A, 200B of a vagus nerve 200 of a mammal. The device 300 may be self-contained, as shown, or comprised of various separate, interconnected units. The control unit 330 may control the electrical impulse generator 310 for generation of a signal suitable for amelioration of the hypotension when the signal is applied via the electrodes 340 to the vagus nerve 200. It is noted that VNS device 300 may be referred to by its function as a pulse generator.

In accordance with one embodiment, one or more electrical impulses are directed to location A on or near the vagus nerve above the cardiac branch. In this embodiment one or more electrical impulses are introduced at the location A to block and/or modulate and/or inhibit up-regulation of the parasympathetic tone and affect an increase in heart function, and possibly a dilation of airways. Location B, for instance, being below the cardiac branch, would have little effect on cardiac performance, but may be used to dilate airways.

In patients known to be subject to shock, such as anaphylactic shock, one or more electrical impulse emitting devices 300 may be implanted in one or more selected regions 200A of the vagus nerve 200. Device 300 may be percutaneous for emergency applications, wherein device 300 may comprise an electrode 340 powered via an external power source 320. U.S. Patent Application Publications 2005/0075701 and 2005/0075702, both to Shafer, both of which are incorporated herein by reference, relating to stimulation of neurons of the sympathetic nervous system to attenuate an immune response, contain descriptions of pulse generators that may be applicable to the present invention.

Figure 4:
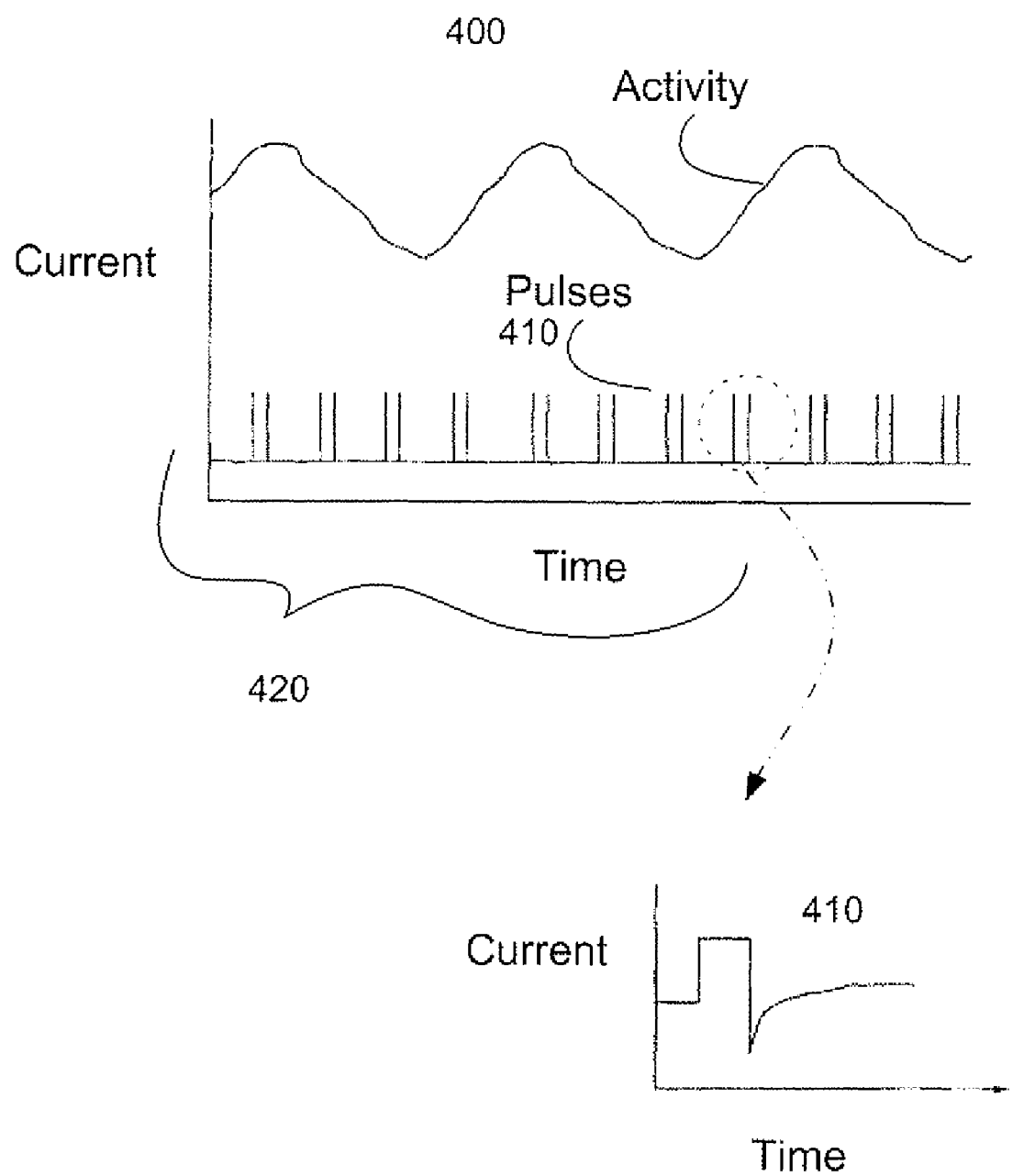
FIG. 4 illustrates an exemplary electrical voltage/current profile for a blocking and/or modulating impulse applied to a portion or portions of the vagus nerve in accordance with an embodiment of the present invention.

FIG. 4 illustrates an exemplary electrical voltage/current profile for a blocking and/or modulating impulse applied to a portion or portions of the vagus nerve in accordance with an embodiment of the present invention.

With reference to FIG. 4, application of a suitable electrical voltage/current profile 400 for the blocking and/or modulating impulse 410 to the portion 200A of the vagus nerve 200 may be achieved using a pulse generator 310. In a preferred embodiment, the pulse generator 310 may be implemented using a power source 320 and a control unit 330 having, for instance, a processor, a clock, a memory, etc., to produce a pulse train 420 to the electrode(s) 340 that deliver the blocking and/or modulating impulse 410 to the nerve 200 via leads 350.

For percutaneous use, the VNS device 300 may be available to the surgeon as external emergency equipment. For subcutaneous use, the VNS device 300 may be surgically implanted, such as in a subcutaneous pocket of the abdomen. The VNS device 300 may be powered and/or recharged from outside the body or may have its own power source 320. By way of example, the VNS device 300 may be purchased commercially. The VNS device 300 is preferably programmed with a physician programmer, such as a Model 7432 also available from Medtronic, Inc.

The parameters of the modulation signal 400 are preferably programmable, such as the frequency, amplitude, duty cycle, pulse width, pulse shape, etc. In the case of an implanted pulse generator, programming may take place before or after implantation. For example, an implanted pulse generator may have an external device for communication of settings to the generator. An external communication device may modify the pulse generator programming to improve treatment.

The electrical leads 350 and electrodes 340 are preferably selected to achieve respective impedances permitting a peak pulse voltage in the range from about 0.2 volts to about 20 volts.

The blocking and/or modulating impulse signal 410 preferably has a frequency, an amplitude, a duty cycle, a pulse width, a pulse shape, etc. selected to influence the therapeutic result, namely blocking and/or modulating some or all of the vagus nerve transmissions. For example the frequency may be about 1 Hz or greater, such as between about 25 Hz to 3000 Hz, or between about 1000 Hz to about 2500 Hz. (These are notably higher frequencies than typical nerve stimulation or modulation frequencies.) The modulation signal may have a pulse width selected to influence the therapeutic result, such as about 20 µS or greater, such as about 20 µS to about 1000 µS. The modulation signal may have a peak voltage amplitude selected to influence the therapeutic result, such as about 0.2 volts or greater, such as about 0.2 volts to about 20 volts.

In accordance with a preferred embodiment, VNS devices 300 in accordance with the present invention are provided in the form of a percutaneous or subcutaneous implant that can be reused by an individual.

In accordance with another embodiment, devices in accordance with the present invention are provided in a "pacemaker" type form, in which electrical impulses 410 are generated to a selected region 200A of the vagus nerve 200 by VNS device 300 on an intermittent basis to create in the patient a lower reactivity of the vagus nerve 200 to up-regulation signals.

In accordance with another embodiment, devices 300 in accordance with the present invention are incorporated in an endotracheal tube device to ameliorate hypotension during surgery. In a preferred embodiment one or more devices 300 are located in the distal portion of an endotracheal tube to contact selected region 200A of the vagus nerve 200 to impart appropriate electrical impulses to dampen reactivity of the vagus nerve 200 to stimulus. In all cases of permanent implantation, however, the implanting surgeon should vary the signal modulated by the control unit 330 and specific location of the lead 350 until the desired outcome is achieved, and should monitor the long-term maintenance of this effect to ensure that adaptive mechanisms in the patient's body do not nullify the intended effects.

In addition, or as an alternative to the devices to implement the modulation unit for producing the electrical voltage/current profile of the blocking and/or modulating impulse to the electrodes, the device disclosed in U.S. Patent Publication No.: 2005/0216062 (the entire disclosure of which is incorporated herein by reference), may be employed. U.S. Patent Publication No.: 2005/0216062 discloses a multi-functional electrical stimulation (ES) system adapted to yield output signals for effecting faradic, electromagnetic or other forms of electrical stimulation for a broad spectrum of different biological and biomedical applications. The system includes an ES signal stage having a selector coupled to a plurality of different signal generators, each producing a signal having a distinct shape such as a sine, a square or a saw-tooth wave, or simple or complex pulse, the parameters of which are adjustable in regard to amplitude, duration, repetition rate and other variables. The signal from the selected generator in the ES stage is fed to at least one output stage where it is processed to produce a high or low voltage or current output of a desired polarity whereby the output stage is capable of yielding an electrical stimulation signal appropriate for its intended application. Also included in the system is a measuring stage which measures and displays the electrical stimulation signal operating on the substance being treated as well as the outputs of various sensors which sense conditions prevailing in this substance whereby the user of the system can manually adjust it or have it automatically adjusted by feedback to provide an electrical stimulation signal of whatever type he wishes and the user can then observe the effect of this signal on a substance being treated.

Prior to discussing experimental results, a general approach to treating hypotension in accordance with one or more embodiments of the invention may include a method of (or apparatus for) treating hypotension associated with anaphylaxis, anaphylactic shock, or some other trigger, comprising applying at least one electrical impulse to one or more selected regions of the vagus nerve of a mammal in need of relief of hypotension.

The method may include: implanting one or more electrodes to the selected regions of the vagus nerve; and applying one or more electrical stimulation signals to the electrodes to produce the at least one electrical impulse. The one or more electrical stimulation signals may be of a frequency between about 1 Hz to 3000 Hz, and have an amplitude of between about 1-6 volts.

The one or more electrical stimulation signals may be of a frequency between about 750 Hz to 1250 Hz; or between about 10 Hz to 35 Hz. The one or more electrical stimulation signals may be of an amplitude of between about 0.75 to 1.5 volts, preferably about 1.0 volts. The one or more electrical stimulation signals may be one or more of a full or partial sinusoid, square wave, rectangular wave, and/or triangle wave. The one or more electrical stimulation signals may have a pulsed on-time of between about 50 to 500 microseconds, such as about 100, 200 or 400 microseconds.

The polarity of the pulses may be maintained either positive or negative. Alternatively, the polarity of the pulses may be positive for some periods of the wave and negative for some other periods of the wave. By way of example, the polarity of the pulses may be altered about every second.

EXPERIMENTAL DATA

While up-regulating the signal provided by the sympathetic nerves may accomplish the desired treatment effect, the present invention suggests that a more direct route to immediately breaking the cycle of hypotension is via the vagus nerve because the mode of action for the hypersensitivity response in hypotension is at the vagus nerve and not through the sympathetic nerves. Therefore, experiments were performed to identify exemplary methods of how electrical signals can be supplied to the peripheral nerve fibers that innervate and/or control the myocardium (and/or vasoconstriction) to (i) reduce the sensitivity of the muscle to the signals of tonic contraction, (ii) to blunt the intensity of, or break the tonic over-contraction once it has been initiated, and/or (iii) to constrict the vessels to increase blood pressure.

In particular, specific signals, selected from within a range of known nerve signals, were applied to the vagus nerves and/or the sympathetic nerves in guinea pigs, to produce selective interruption or reduction in the effects of vagal nerve activity leading to attenuation of histamine-induced hypotension and bronchoconstriction.

Experimental Procedure 1:

Male guinea pigs (400 g) were transported to the lab and immediately anesthetized with an i.p. injection of urethane 1.5 g/kg. Skin over the anterior neck was opened and the carotid artery and both jugular veins were cannulated with PE50 tubing to allow for blood pressure/heart rate monitoring and drug administration, respectively. The trachea was cannulated and the animal ventilated by positive pressure, constant volume ventilation followed by paralysis with succinylcholine (10 ug/kg/min) to paralyze the chest wall musculature to remove the contribution of chest wall rigidity from airway pressure measurements.

Guanethidine (10 mg/kg i.v.) was given to deplete norepinephrine from nerve terminals that may interfere with vagal nerve stimulation. Both vagus nerves were exposed in the neck and connected to electrodes to allow selective stimuli of these nerves. Following 15 minutes of stabilization baseline hemodynamic and airway pressure measurements were made before and after the administration of repetitive doses of i.v. histamine.

Following the establishment of a consistent response to i.v. histamine, vagal nerve stimulation was attempted at variations of frequency, voltage and pulse duration to identify parameters that attenuate responses to i.v. histamine. Hypotension and bronchoconstriction in response to i.v. histamine are known to be due both to direct muscle effects and to stimulation of vagal nerves to release acetylcholine.

At the end of vagal nerve challenges, atropine was administered i.v. before a subsequent dose of histamine to determine what percentage of the histamine-induced hypotension and bronchoconstriction was vagal nerve induced. This was considered a 100% response. Success of electrical interruption in vagal nerve activity in attenuating histamine-induced hypotension and bronchoconstriction was compared to this maximum effect. Euthanasia was accomplished with intravenous potassium chloride.

The blood pressure and heart rate were measured to track the subjects' vital signs. In order to measure the bronchoconstriction, the airway pressure was measured with two sensors. In all the following graphs, the top line BP (red) shows blood pressure, second line AP1 (green) shows airway pressure, third line AP2 (blue) shows airway pressure on another sensor, the last line HR is the heart rate derived from the pulses in the blood pressure.

Figure 5:
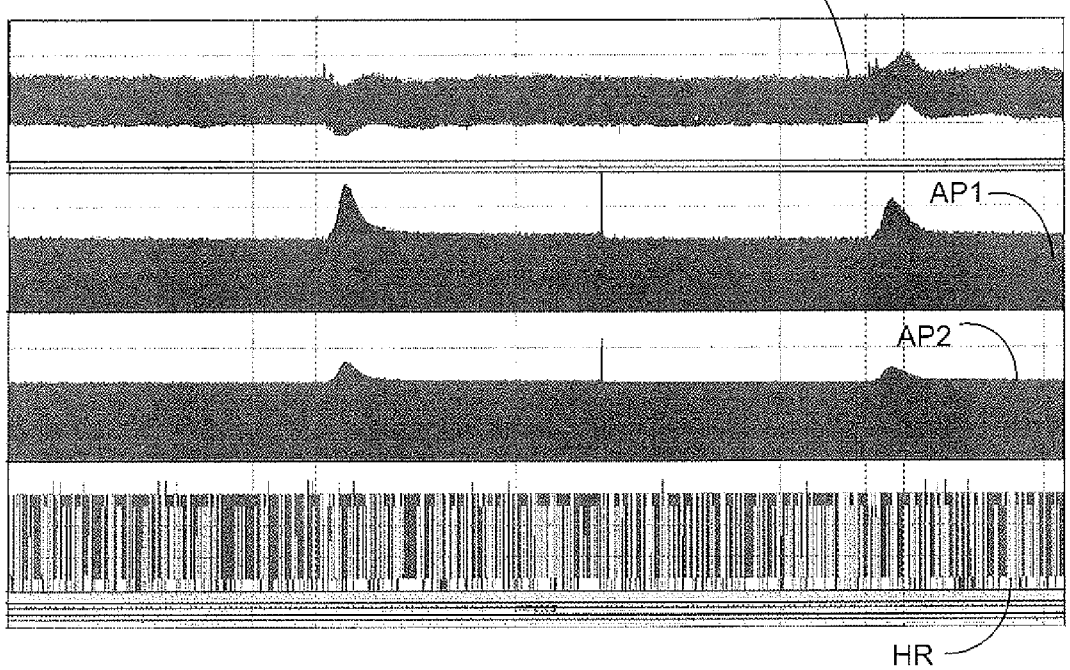
FIGS. 5-13 graphically illustrate exemplary experimental data obtained in accordance with multiple embodiments of the present invention.

FIG. 5 graphically illustrates exemplary experimental data on guinea pig #5. The graphs of FIG. 5 show the effect of a 25 Hz, 400 μS, 1V square wave signal applied to both left and right vagus nerve in guinea pig #5 when injected with 8 μg/kg histamine to decrease blood pressure and increase airway pressure. The first trough and peak, respectively, in blood and airway pressures are from histamine alone, the next peak and peak, respectively, are histamine and signal applied. The blood pressure is clearly increased, but the heart rate is not affected, by the 25 Hz, 400 μS, 1V square-wave signal on the vagus nerve. It also is clearly shown that the increase in airway pressure due to histamine is reduced in the presence of the 25 Hz, 400 μS, 1V square wave on the vagus nerve.

Figure 6:
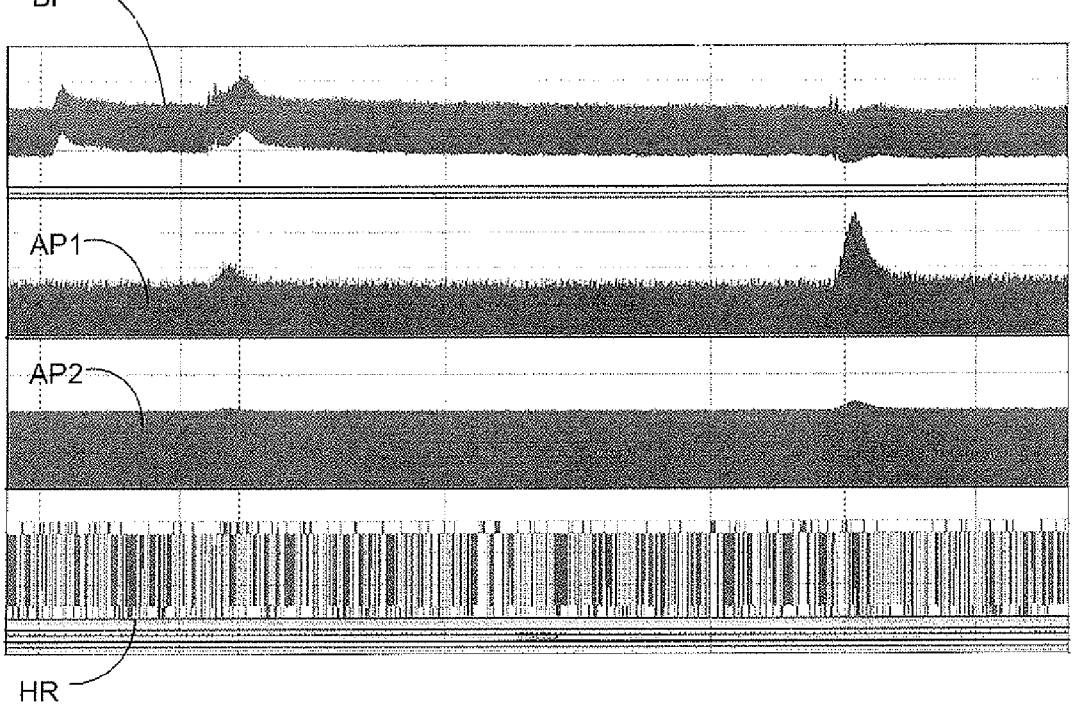

FIG. 6 graphically illustrates additional exemplary experimental data on guinea pig #5. The graphs of FIG. 6 show the effect of a 25 Hz, 200 μS, 1V square wave signal applied to both of the left and right vagus nerves in guinea pig #5 when injected with 8 μg/kg histamine. The first blood pressure peak, without an effect on airway pressure, is signal alone. The second peak and peak, respectively, are from histamine and signal applied simultaneously, whereas the third trough and peak, respectively, are from histamine alone. The blood pressure clearly is increased by the 25 Hz, 200 μS, 1V square wave signal, without simply driving the heart rate higher (i.e., heart pumping stronger, not faster or constriction of blood vessels). It also is shown clearly that the increase in airway pressure due to histamine is reduced in the presence of the 25 Hz, 200 μS, 1V square wave on the vagus nerve. It is clear that the blood pressure increase and airway pressure reduction are even better with the 200 μS pulse width than the 400 μS signal.

Figure 7:
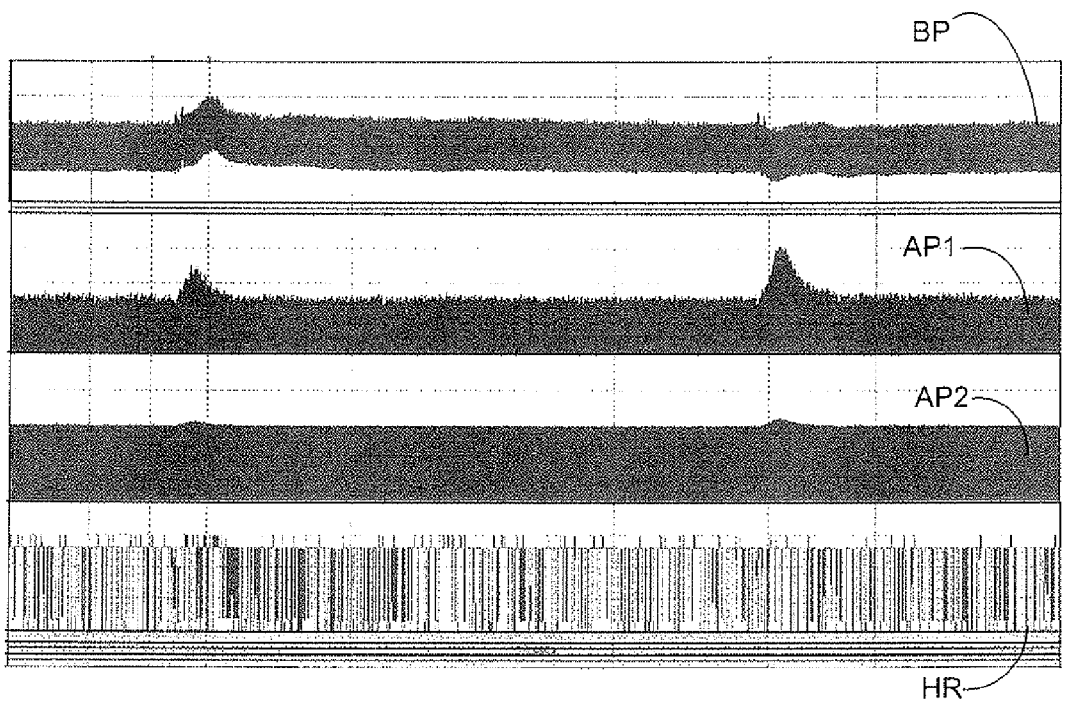

FIG. 7 graphically illustrates further exemplary experimental data on guinea pig #5. The graphs of FIG. 7 show repeatability of the effect seen in the previous graph. The animal, histamine and signal are the same as the graphs in FIG. 6.

It is significant that the effects shown above were repeated several times with this animal (guinea pig #5), without any loss of nerve activity observed. We could move the electrodes proximally and distally along the vagus nerve and achieve the same effect. It was, therefore, concluded that the effect was being achieved by means other than simply damaging the nerve.

Figure 8:
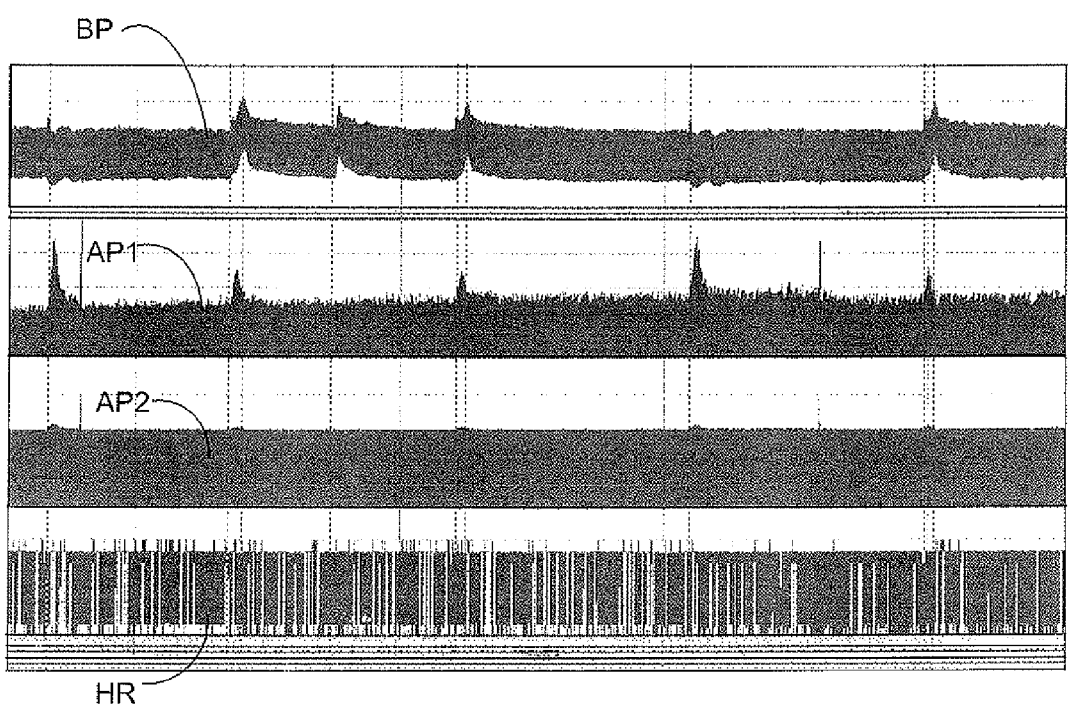

FIG. 8 graphically illustrates subsequent exemplary experimental data on guinea pig #5. The graphs of FIG. 8 show the effect of a 25 Hz, 100 μS, 1V square wave that switches polarity from + to − voltage every second. This signal is applied to both left and right vagus nerve in guinea pig #5 when injected with 8 μg/kg histamine. From left to right, the vertical dotted lines coincide with blood pressure/ airway events associated with: (1) histamine alone (blood pressure trough with a large airway spike—followed by a very brief manual occlusion of the airway tube); (2) histamine with a 200 μS signal applied (blood pressure peak with a smaller airway spike); (3) a 100 μS electrical signal alone (blood pressure peak with no airway spike); (4) histamine with a 100 μS signal applied (blood pressure peak with a smaller airway spike again); (5) histamine alone (blood pressure trough with a large airway spike); and (6) histamine with the 100 μS signal applied (blood pressure peak with a smaller airway spike again).

The animal's blood pressure is substantially increased by this signal, but as with the prior animal (guinea pig #4), the heart rate is not affected. The blood and airway pressure effects appear to be better with the 100 μS pulse width than the 200 μS pulse width signal. This evidence strongly suggests that the decrease in blood pressure due to histamine can be effectively negated and overcome by the application of a 25 Hz, 100 μs, 1V square wave with alternating polarity on the vagus nerve. This evidence also strongly suggests that the respective the increase in airway pressure can be significantly reduced by the application of a 25 Hz, 100 μS, 1V square wave with alternating polarity on the vagus nerve.

Figure 9:
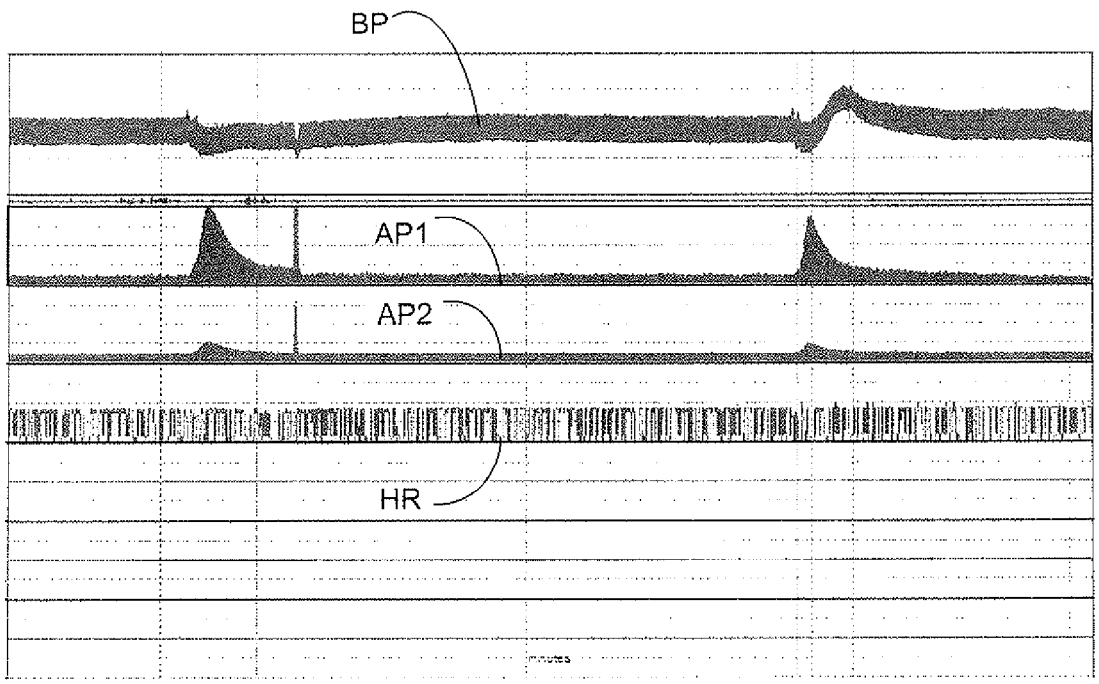

FIG. 9 graphically illustrates exemplary experimental data on guinea pig #6. The graphs in FIG. 9 show the effect of a 25 Hz, 200 μS, 1V square wave that switches polarity from + to − voltage every second. This signal is applied to both left and right vagus nerve in guinea pig #6 when injected with 16 μg/kg histamine. Note that this animal demonstrated a very high tolerance to the effects of histamine, and therefore was not an ideal test subject for the histamine-induced effects. However, the animal did provide us with the opportunity to test the signal-only effects on blood pressure and modification of signal parameters.

In this case, the first trough in blood pressure and peak in airway pressure are from histamine alone, followed by a trough-peak pair corresponding to a brief manual occlusion of the airway. The next and final trough-then-peak of the blood pressure, accompanied by a peak in the airway pressure, is histamine with the signal applied. It is clearly shown that the blood pressure is increased by application of a 25 Hz, 200 µS, 1V square-wave signal with alternating polarity on the vagus nerve, but again, the heart rate is not affected. Furthermore, the increase in airway pressure due to histamine is reduced moderately in its peak, and most definitely in its duration, when in the presence of the 25 Hz, 200 µS, 1V square wave with alternating polarity on the vagus nerve.

Figure 10:
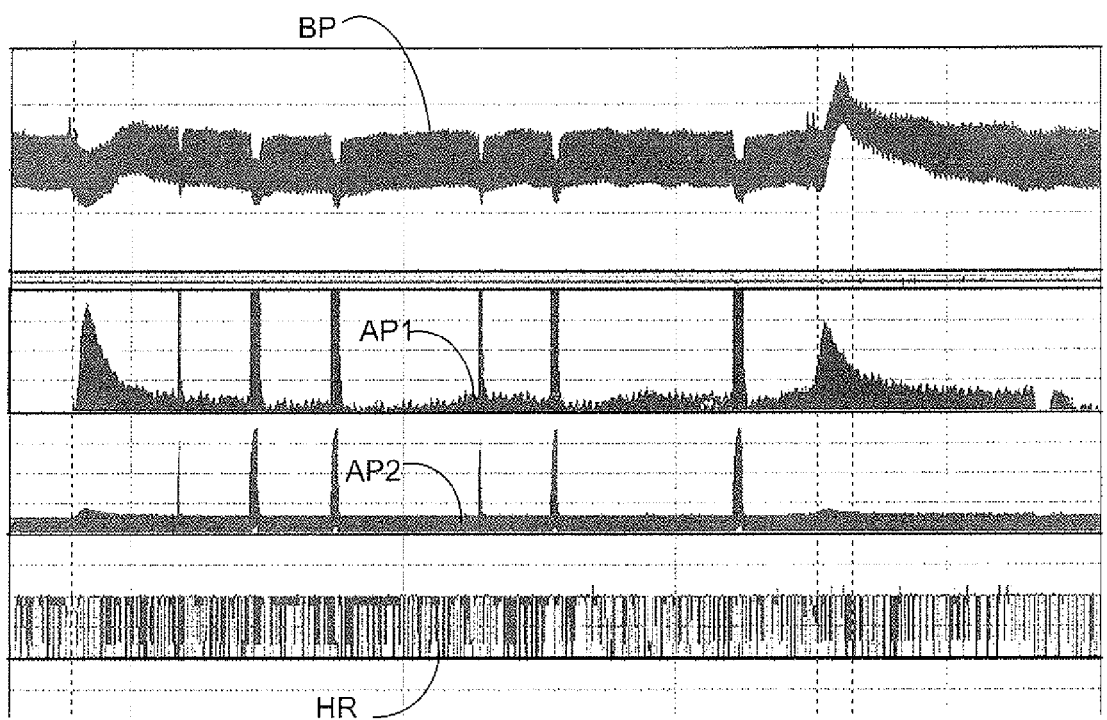

FIG. 10 graphically illustrates additional exemplary experimental data on guinea pig #6. As mentioned above, guinea pig #6 in the graphs of FIG. 9 above needed more histamine than other guinea pigs (16-20 µg/kg vs 8 µg/kg) to achieve the desired increase in airway pressure. Also, the beneficial effects of the 1V signal were less pronounced in pig #6 than in #5. Consequently, we tried increasing the voltage to 1.5V. The first blood pressure trough and airway pressure peak is from histamine alone. A series of six manual occlusions of the airway tube followed, each causing a blood pressure trough and airway pressure spike. The next and final blood pressure trough-then-peak and airway pressure peak are the result of histamine with the 1.5V, 25 Hz, 200 µS alternating polarity signal. The beneficial effects on the blood pressure, as well as the airway pressure, are seen with slightly more impact, but not substantially better than the 1V.

Figure 11:
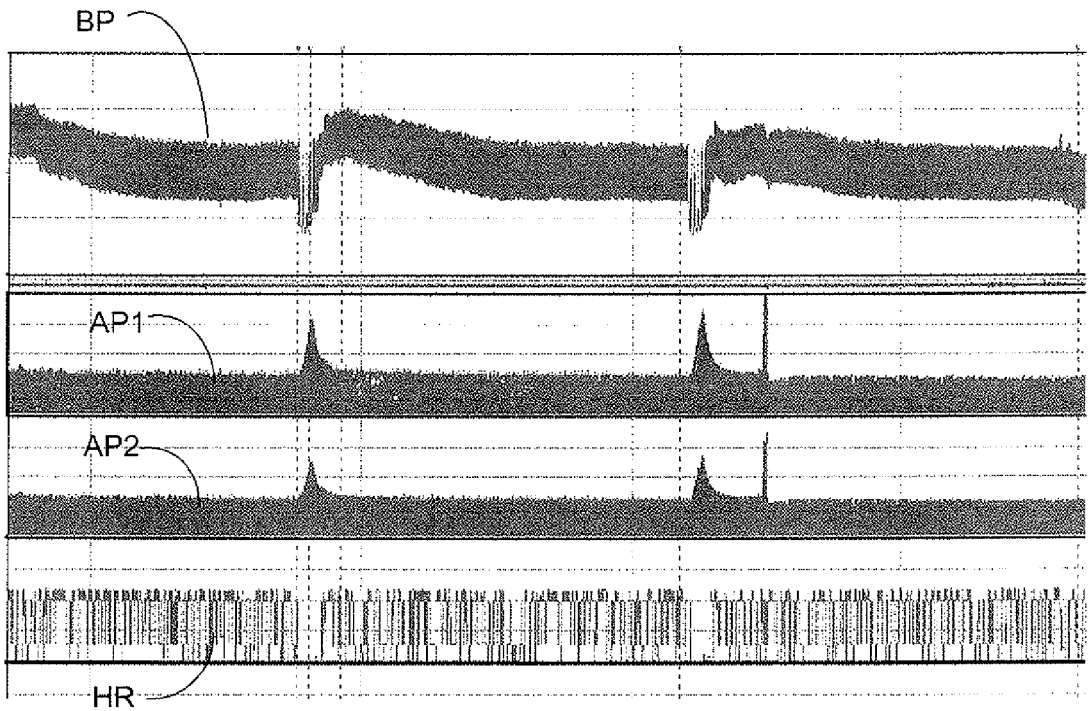

FIG. 11 graphically illustrates further exemplary experimental data on guinea pig #6. Since guinea pig #6 was losing its airway reaction to histamine, we tried to determine if the 25 Hz, 200 µS, 1V, alternating polarity signal could mitigate the effects of a 20V, 20 Hz airway pressure stimulating signal to produce a simulated asthmatic or shock-like response. The first event of a blood pressure trough and an airway pressure peak corresponds to the 20V, 20 Hz stimulator signal applied to simulate shock, then switched over to the 25 Hz, 200 µS, 1V, alternating polarity signal, causing the blood pressure to peak. The second event is the 20V, 20 Hz signal alone, causing a major but rebounding blood pressure trough and an airway pressure peak.

The blood pressure increase after application of the Hz, 200 µS, 1V signal during the first event caused a visible benefit over no signal during the second event. Overall, the effects of the first event look modestly reduced and narrower than those of the second event. The 25 Hz, 200 µS, 1V signal may have some beneficial airway pressure reduction after electrical stimulation of airway constriction. Notably, in both the first and second events, the simulated shock-signal momentarily interfered with the heart rate, until equilibrium could again be reached. After the second event, a brief manual occlusion occurred, spiking the airway pressure and depressing the blood pressure.

On animal #6 we investigated which branch of the vagus nerve had the most effect on the blood pressure. We found that the right branch stimulated with the 25 Hz, 1V, 200 µS signal was responsible for the vast majority of the blood pressure increase. Stimulating the left vagus did not measurably affect the blood pressure.

Figure 12:
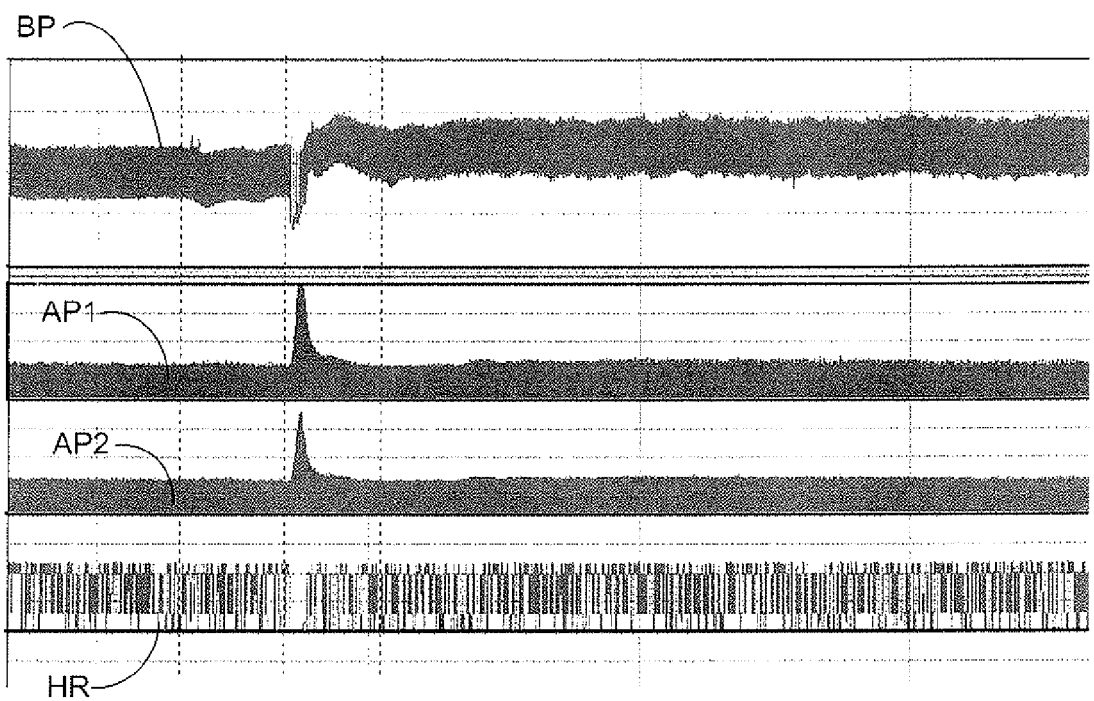

FIG. 12 graphically illustrates subsequent exemplary experimental data. On guinea pig #6 we also investigated the effect of the 1V, 25 Hz, and 200 µS alternating polarity signal on blood pressure. After a brief application of histamine and the asthma/shock-simulating signal, causing a corresponding blood pressure trough and airway pressure peak, the 1V, 25 Hz, and 200 µS alternating polarity signal was applied for 10 minutes. The charts show the sustained increase in blood pressure throughout the 10-minute signal application. Even after application of the signal for 10 minutes continuously, there was no loss of nerve conduction or signs of damage.

In contrast to the previous animals, guinea pig #7 was in distress from the initial preparation before any tests were run. Its blood pressure was low and sinking while the airway pressure was uneven and rising. This animal's blood pressure could be raised with our 25 Hz, 1V, 200 µS signal but without the signal, it kept falling. When the blood pressure was almost gone, we kept our signal on for several minutes and kept the animal alive for that time.

Figure 13:
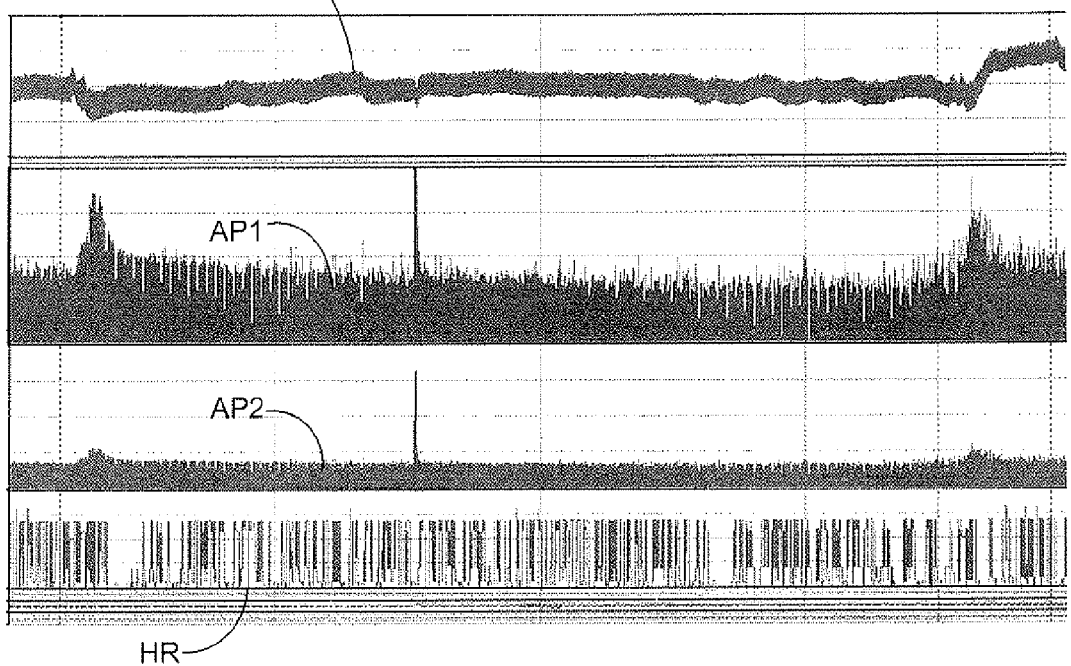

FIG. 13 graphically illustrates exemplary experimental data on guinea pig #8. The graph below shows the effect of a 25 Hz, 200 µS, 1V square wave that switches polarity from + to − voltage every second. This signal is applied to both left and right vagus nerve in guinea pig #8 when injected with 12 µg/kg histamine. The first trough-peak pair in blood and airway pressures is from histamine alone, whereas the next trough-peak pair represents a manual occlusion. The third pair, a blood pressure trough-then-peak and an airway pressure peak, is histamine with the signal applied. The blood pressure is clearly increased by this signal, 25 Hz, 200 µS, 1V square wave with alternating polarity, but the heart rate is not affected. It clearly is shown also that the increase in airway pressure due to histamine is reduced in the presence of the 25 Hz, 200 µS, 1V square wave with alternating polarity on the vagus nerve. We have reproduced this effect multiple times, on 4 different guinea pigs, on 4 different days.

The blood pressure in guinea pigs can be significantly increased by applying appropriate electrical signals to the vagus nerve. Likewise, airway constriction induced by histamine in guinea pigs can be significantly reduced by applying appropriate electrical signals to the vagus nerve.

With a 25 Hz, 1V, 100-200 µS signal applied to the right branch or both branches of vagus nerve, a significant increase in guinea pig blood pressure is observed. This has been repeated on multiple animals many times. There is no evidence of nerve damage. Such a signal may be applied in the treatment of low blood pressure in conditions such as septic shock and anaphylactic shock.

The 25 Hz, 1V, 100-200 µS signal applied to the vagus nerve also significantly reduced airway constriction due to histamine.

Application of the signal to the vagus nerve appears to have some effects lasting long after the signal is removed. Specific, repeatable experimentation may be done to substantiate these longer lasting effects.

Additional testing on the guinea pig model may quantify the extent to which longer lasting effects remain after stimulation is removed.

Experimental Procedure 2

In U.S. patent application Ser. No. 10/990,938 filed Nov. 17, 2004 (Publication Number US2005/0125044A1), Kevin J. Tracey proposes a method of treating many diseases including, among others, asthma, anaphylactic shock, sepsis and septic shock by electrical stimulation of the vagus nerve. However, the examples in the Tracey application use an electrical signal that is 1 to 5V, 1 Hz and 2 mS to treat endotoxic shock, and no examples are shown that test the proposed method on an asthma model, an anaphylactic shock model, or a sepsis model. The applicants of the present application performed additional testing to determine if Tracey's proposed method has any beneficial effect on blood pressure or bronchial constriction. The testing followed the model described above, which demonstrated the efficacy of the method used in accordance with the present application. The applicants of the present application sought to determine whether Tracey's signals can be applied to the vagus nerve in guinea pigs to increase blood pressure and/or attenuate histamine-induced bronchoconstriction.

Male guinea pigs (400 g) were transported to the lab and immediately anesthetized with an i.p. injection of urethane 1.5 g/kg. Skin over the anterior neck was opened and the carotid artery and both jugular veins are cannulated with PE50 tubing to allow for blood pressure/heart rate monitoring and drug administration, respectively. The trachea was cannulated and the animal ventilated by positive pressure, constant volume ventilation followed by paralysis with succinylcholine (10 ug/kg/min) to paralyze the chest wall musculature to remove the contribution of chest wall rigidity from airway pressure measurements.

Guanethidine (10 mg/kg i.v.) was given to deplete norepinephrine from nerve terminals that may interfere with vagal nerve stimulation. Both vagus nerves were exposed and connected to electrodes to allow selective stimuli of these nerves. Following 15 minutes of stabilization, baseline hemodynamic and airway pressure measurements were made before and after the administration of repetitive doses of i.v. histamine.

Following the establishment of a consistent response to i.v. histamine, vagal nerve stimulation was attempted at variations of 1 to 5 volts, 1 Hz, 2 mS to identity parameters that attenuate responses to i.v. histamine. Bronchoconstriction in response to i.v. histamine is known to be due to both direct airway smooth muscle effects and due to stimulation of vagal nerves to release acetylcholine.

At the end of vagal nerve challenges atropine was administered i.v. before a subsequent dose of histamine to determine what percentage of the histamine-induced bronchoconstriction was vagal nerve induced. This was considered a 100% response. Success of electrical interruption in vagal nerve activity in attenuating histamine-induced bronchoconstriction was compared to this maximum effect. Euthanasia was accomplished with intravenous potassium chloride.

The blood pressure and heart rate were measured to track the subjects' vital signs. In order to measure the bronchoconstriction, the airway pressure was measured in two places. In all the following graphs, the top line BP (red) shows blood pressure, second line AP1 (green) shows airway pressure, third line AP2 (blue) shows airway pressure on another sensor, the last line HR is the heart rate derived from the pulses in the blood pressure.

Figure 14:
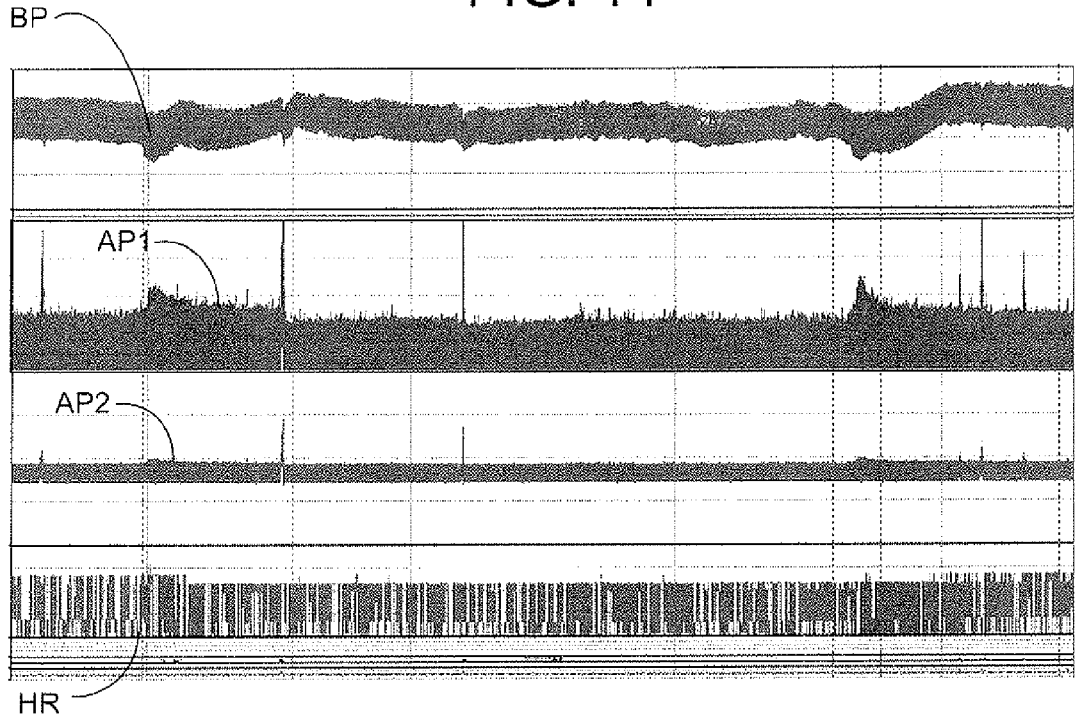
FIGS. 14-19 graphically illustrate the inability of signals taught by U.S. patent application Ser. No. 10/990,938 to achieve the results of the present invention.

FIG. 14 graphically illustrates exemplary experimental data from a first experiment on another guinea pig. The graph shows the effects of Tracey's 1V, 1 Hz, 2 mS waveform applied to both vagus nerves on the guinea pig. The first trough in blood pressure, corresponding to a first peak in airway pressure, is from histamine alone, followed by a brief manual occlusion, after which Tracey's signal was applied for 10 minutes as proposed in Tracey's patent application. As seen from the second histamine-induced blood pressure trough and airway pressure peak, at the right of the graph, the signal has no noticeable effect on blood pressure or airway pressure. The blood pressure actually rose after the signal was turned off.

Figure 15:
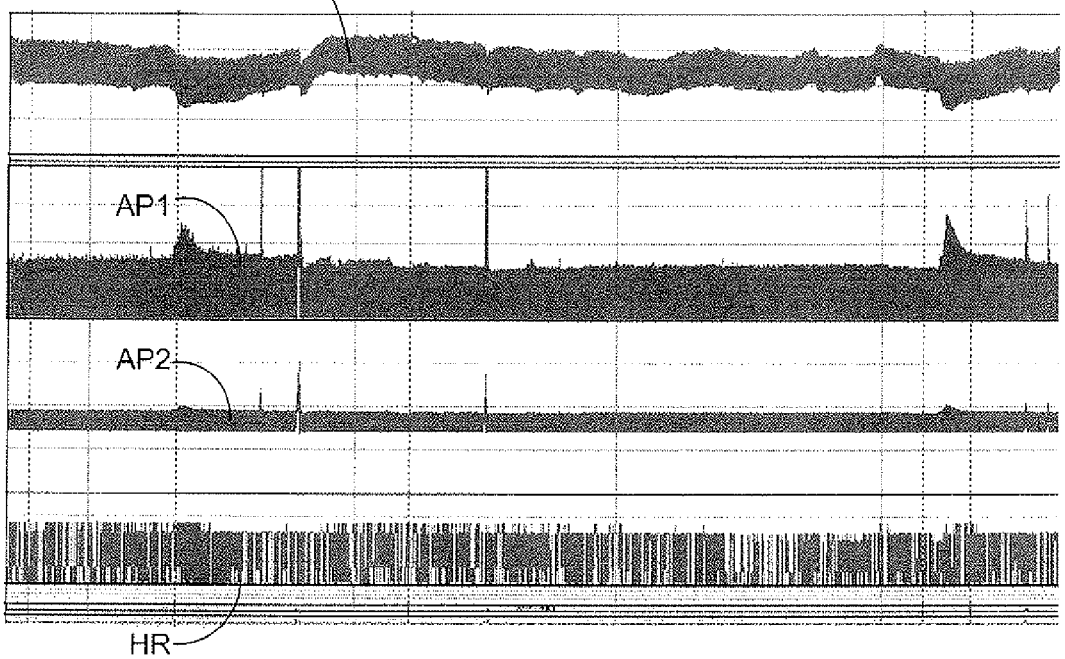

FIG. 15 graphically illustrates exemplary experimental data from a second experiment on the guinea pig in FIG. 14. The graph shows the effects of Tracey's 1V, 1 Hz, 2 mS waveform with the polarity reversed (Tracey did not specify polarity in the patent application) applied to both vagus nerves on the guinea pig. Again, the signal has no beneficial effect on blood or airway pressure. In fact, during application of the signal, the blood pressure was slightly lower, and the signal did not keep the blood pressure from falling when the histamine was applied. Moreover, the second airway peak from the signal and histamine combination is actually higher than the first peak of histamine alone.

Figure 16:
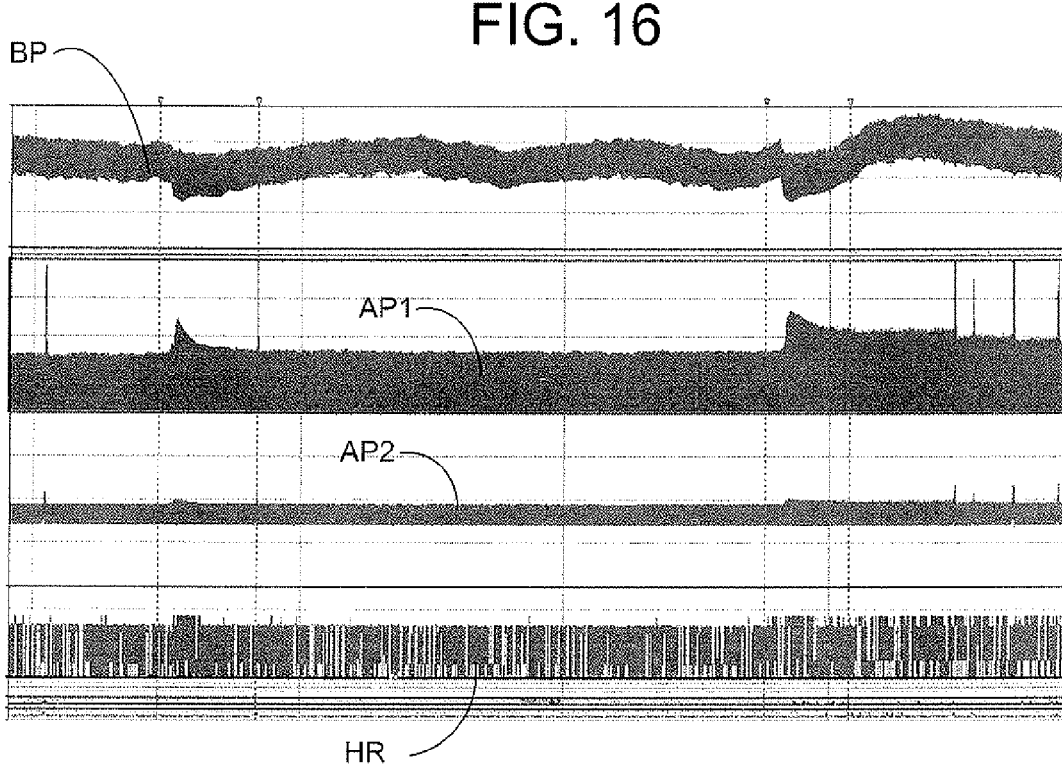

FIG. 16 graphically illustrates exemplary experimental data from a third experiment on the guinea pig in FIG. 14. The graph shows the effects of Tracey's 1V, 1 Hz, 2 mS waveform applied to both vagus nerves on the guinea pig. Again, the signal has no beneficial effect on blood or airway pressure. Analogous to the results in FIG. 15, the signal did not maintain the blood pressure when the histamine was applied. Instead, it increases airway pressure and reduces blood pressure.

Figure 17:
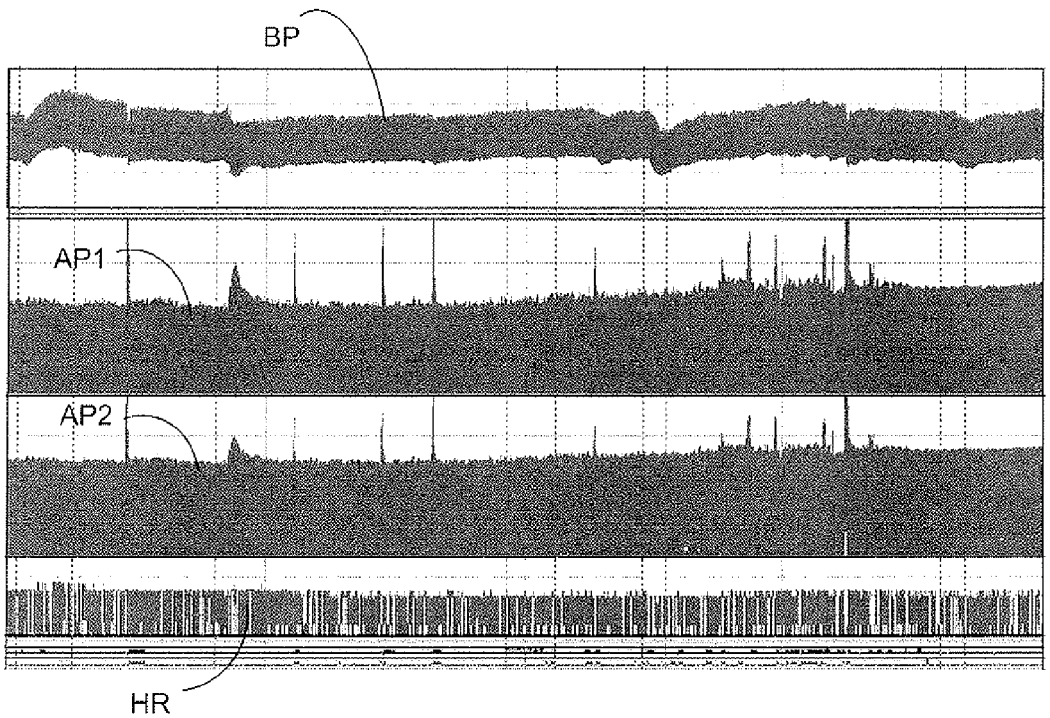

FIG. 17 graphically illustrates additional exemplary experimental data from an experiment on a subsequent guinea pig. The graph shows, from left to right, first a beneficial blood pressure increase from the 1.2V, 25 Hz, 0.2 mS signal disclosed in the present application. The subsequent three electrical stimulation treatments are 1V, 5V, and 2.5V variations of Tracey's proposed signal. It is clear that the Tracey signals do not cause an increase in blood pressure, but rather frequently cause a decrease.

Figure 18:
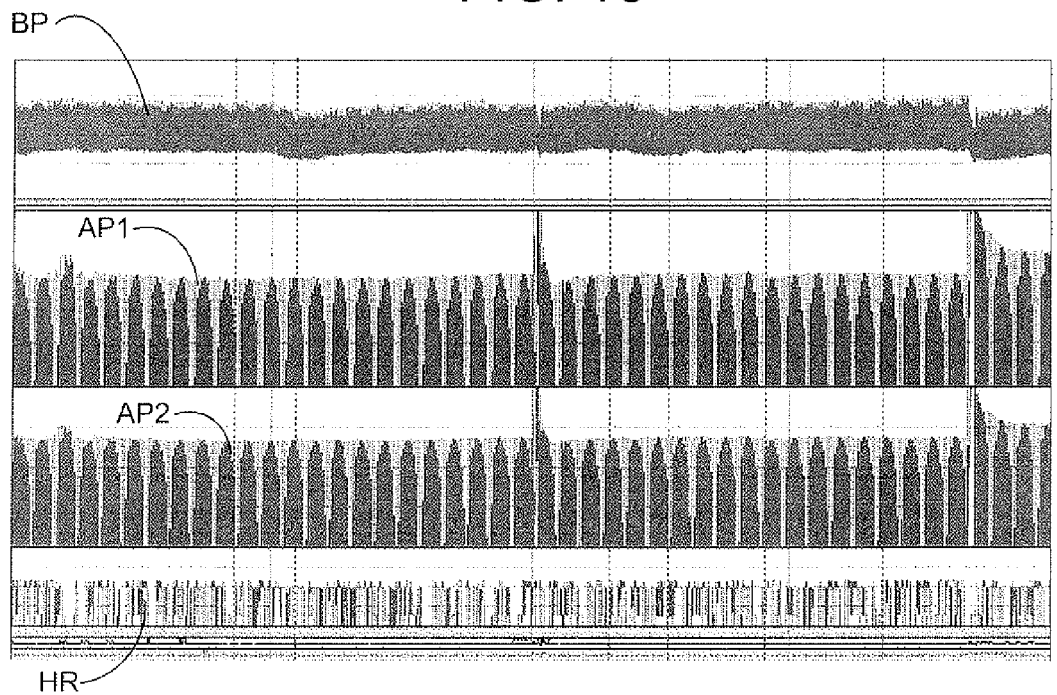

FIG. 18 graphically illustrates further exemplary experimental data from additional experiments using signals within the range of Tracey's proposed examples. None of the signals proposed by Tracey had any beneficial effect on blood pressure. Factoring in a potential range of signals, one experiment used 0.75V, which is below Tracey's proposed range, but there was still no beneficial effect on blood pressure.

Figure 19:
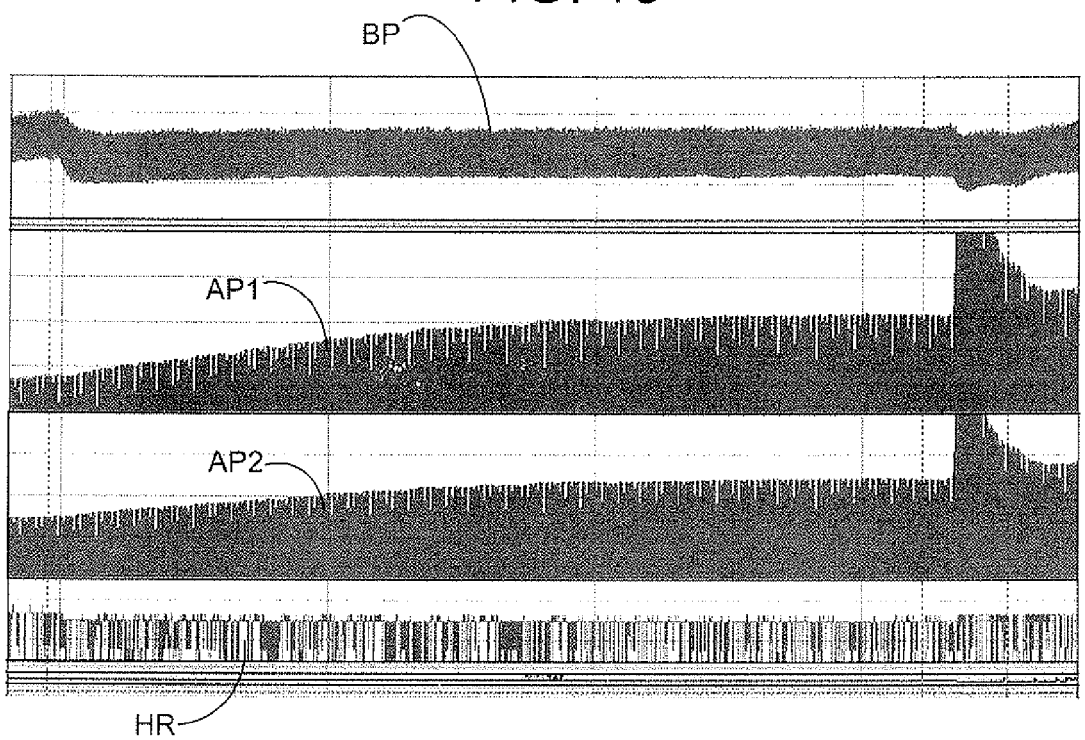

FIG. 19 graphically illustrates exemplary experimental data from subsequent experiments showing the effect of Tracey's 5V, 1 Hz, 2 mS signal on histamine response. The blood pressure fell with application of the Tracey signal and fell even farther with application of the histamine. It is clear that the airway pressure increase is even greater with the signal, and that blood pressure is decreased by the signal.

The full range of the signal proposed by Tracey in his patent application was tested in the animal model of the present application. No reduction in airway pressure was seen. No increase in blood pressure was seen. Most of the voltages resulted in detrimental decreases in blood pressure and detrimental increases in airway pressure.

Experimental Procedure 3

While the above experiments were conducted by inducing hypotension (and/or bronchial constriction) using i.v. histamine, additional test data were obtained in response to anaphylaxis. Fifteen male guinea pigs (400 g) were sensitized by the intraperitoneal injection of ovalbumin (10 mg/kg i.p. every 48 hrs for three doses). Three weeks later animals were transported to the lab and immediately anesthetized with an i.p. injection of urethane 1.5 g/kg. Skin over the anterior neck was opened and the carotid artery and both jugular veins were cannulated with PE50 tubing to allow for blood pressure/heart rate monitoring and drug administration, respectively. The trachea was cannulated and the animal ventilated by positive pressure, constant volume ventilation followed by paralysis with succinylcholine (10 ug/kg/min) to paralyzed chest wall musculature to remove the contribution of chest wall rigidity from airway pressure measurements. Both vagus nerves were isolated and connected to shielded electrodes to allow selective stimuli of these nerves in the manner disclosed in the one or more embodiments disclosed above. Following fifteen minutes of stabilization, baseline hemodynamic and airway pressure measurements were made before and after the administration of increasing concentrations of ovalbumin (0.001-1.0 mg/kg i.v.). Following the increase in airway pressure and hypotension accompanying the anaphylactic response, vagal nerve modulation was made at variations of frequency, voltage and pulse duration to identity parameters that attenuate the hypotensive and bronchoconstrictive responses. Euthanasia was accomplished with intravenous potassium chloride.

Figure 20:
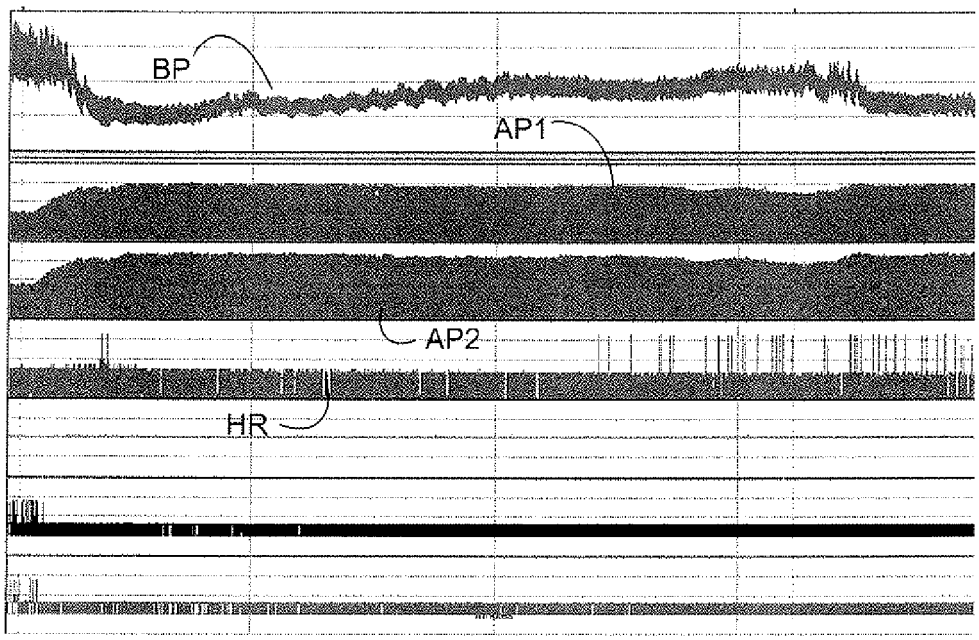
FIGS. 20-22 graphically illustrate exemplary experimental data obtained for the treatment of anaphylaxis according to the present invention.

With reference to FIG. 20, the top line (BP) shows blood pressure, the second line shows airway pressure (AP1), the third line shows airway pressure (AP2) on another sensor, the fourth line is the heart rate (HR) derived from the pulses in the blood pressure. As a baseline of the anaphylactic reaction that is achieved in this model, the first guinea pig's response to the ovalbumin was recorded without any electrical stimulation. The graph in FIG. 20 shows the effect of an injection of 0.75 mg of ovalbumin. About five minutes after the injection, the blood pressure dropped from 125 to 50 mmHg while the airway pressure increased from 11 to 14 cm $H_2O$. This effect was sustained for over sixty (60) minutes with the blood pressure showing some recovery to 90 mmHg.

Figure 21:
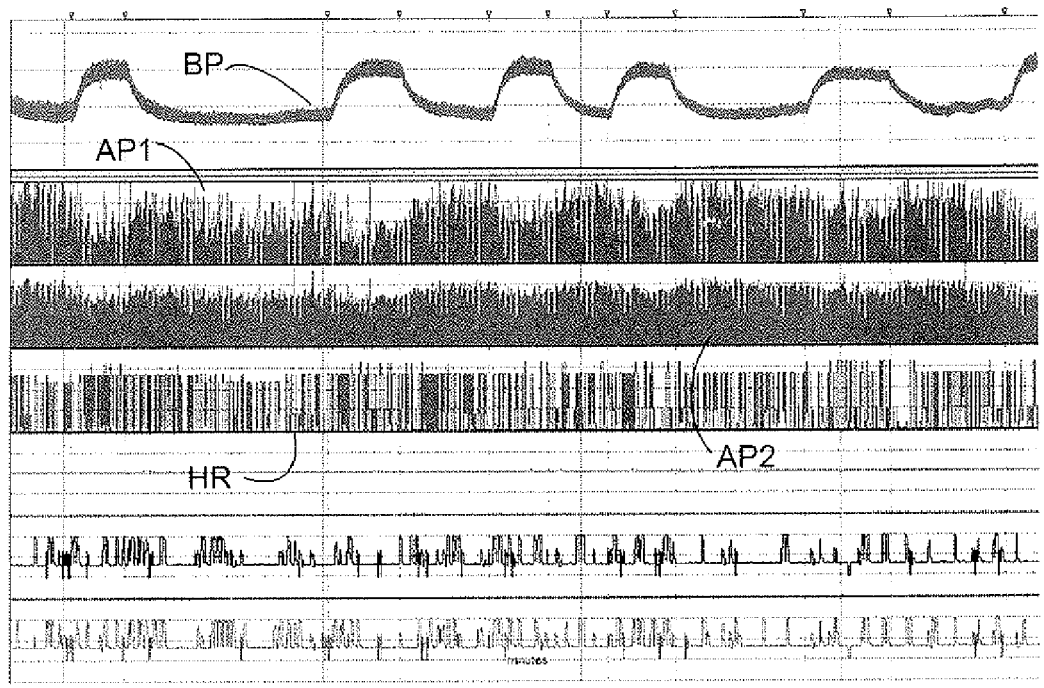

With reference to FIG. 21, another animal (guinea pig #2) was tested to determine the effect of the signals that were shown to be effective in the histamine induced asthma model (Experimental Procedure 1 above). FIG. 21 demonstrates the effect of a 25 Hz, 200 µS, 1.25V square wave signal applied simultaneously to both left and right vagus nerves in sensitized guinea pig #2 after injection with 1.125 mg ovalbumin to cause an anaphylactic response. The larger dose was used to cause a more severe reaction. Starting from the left side of the graph, it may be seen that before electrical stimulation, the blood pressure was severely depressed at 30 mmHg while the airway pressure was almost 22 cm $H_2O$ (9.5 cm increase over baseline). The first peak in blood pressure coincides with the electrical signal applied to the vagus—the blood pressure increased to 60 mmHg (a 100% increase) while the airway pressure reduced by 6.5 cm to about 15.5 cm $H_2O$ (a 68% reduction). The next peak shows the effect repeated. The other peaks show the effects of changing the signal voltage—lowering the voltage results in reduced effectiveness.

Figure 22:
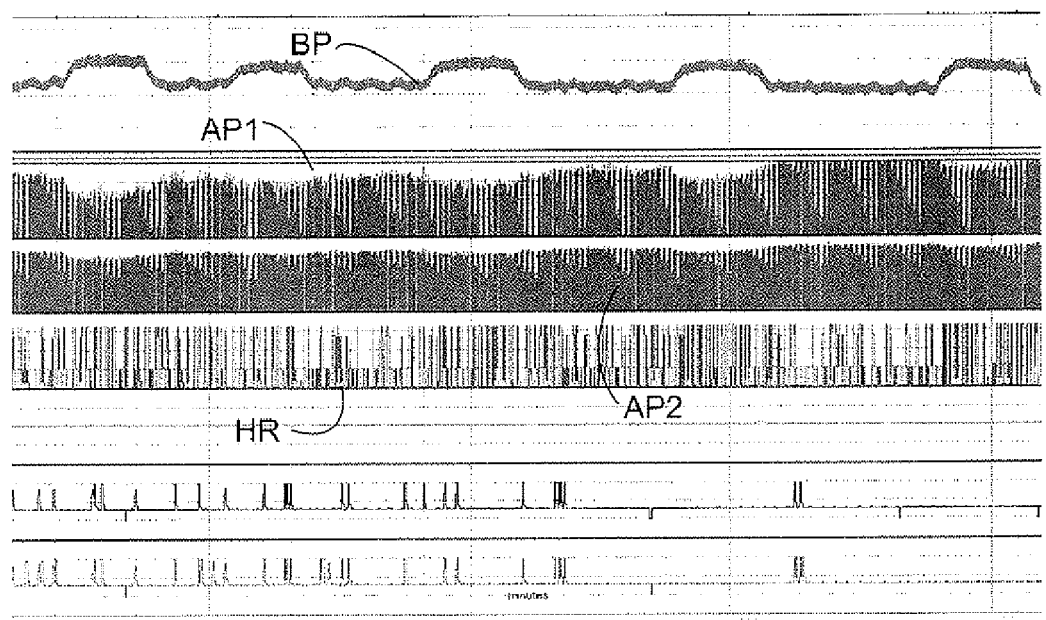

With reference to FIG. 22, the effect of changing the signal frequency and pulse width on blood pressure and airway pressure is shown. The first peak in blood pressure coincides with a 15 Hz, 300 µS, 1.25V electrical signal applied to both sides of the vagus—the blood pressure was increased to 60 mmHg (a 70% increase) while the airway pressure was reduced by 1.5 cm to about 17 cm $H_2O$ (a 25% reduction). The next peak demonstrates a 10 Hz signal—the beneficial effects are reduced compared to 15 Hz. The other peaks show the effects of changing the signal frequency and pulse width—lowering the frequency below 15 Hz or lowering the pulse width below 200 µS results in reduced effectiveness. The signals between 15-25 Hz, and 200-300 µS maintain about the same effectiveness in decreasing the hypotensive and bronchoconstrictive symptoms of anaphylaxis.

Conclusions that may be drawn from the above experimental data include: (1) That the airway constriction and hypotension caused by anaphylaxis in guinea pigs can be significantly reduced by applying appropriate electrical signals to the vagus nerve. (2) That signals from 15 Hz to 25 Hz, 200 µS to 300 µS, and 1.0V to 1.5V were equally effective. (3) That a 25 Hz, 200 µS, 1.25V signal applied to the vagus nerve, airway constriction due to anaphylaxis was reduced up to 68%. This effect has been repeated on several animals. (4) That the 25 Hz, 200 µS, 1.25V signal applied to the vagus nerve produces up to a 100% increase in blood pressure in an anaphylactic guinea pig experiencing severe hypotension. This effect has been repeated on several animals. This may have applications in the treatment of other low blood pressure conditions such as septic shock. (5) That there is some evidence that the application of the signal to the vagus nerve may have the ability to shorten the duration of an anaphylactic episode.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of treating a patient with a disorder comprising:
    positioning an electrode at a target region comprising parasympathetic nerves within or on the patient; and applying at least one electrical impulse to the electrode such that increased blood pressure is achieved in the patient, wherein the electrical impulse has a frequency of between about 10 to 50 Hz.

2. The method of claim 1 wherein the frequency is between about 15 to 30 Hz.

3. The method of claim 1 wherein the frequency is about 25 Hz.

4. The method of claim 1 wherein the electrical impulse has an amplitude of between about 0.2 volts to 20 volts.

5. The method of claim 1 wherein the electrical impulse has a pulsed-on time of between about 200-400 microseconds.

6. The method of claim 1 wherein the electrical impulse has a pulsed-on time of about 200 microseconds.

7. The method set forth in claim 1 wherein the target region comprises a region of the parasympathetic nervous system.

8. The method of claim 1 wherein the target region comprises a region of the vagus nerve proximal to the cardiac branch of the vagus nerve.

9. The method set forth in claim 1 wherein increased blood pressure is achieved by at least one of:
    increasing heart function; and controlling vasoconstriction.

10. The method set forth in claim 9 wherein increasing heart function includes increasing blood pressure and maintaining a stable heart rate.

11. The method of claim 1 wherein the disorder is hypotension.

12. The method of claim 11 wherein the disorder is hypotension associated with shock.

13. A method of treating a patient with a disorder comprising:
    positioning an electrode at a target region comprising parasympathetic nerves within or on the patient; and
    applying at least one electrical impulse to the electrode to a target region in the patient such that increased blood pressure is achieved in the patient without a substantial change in heart rate.

14. The method of claim 13 wherein the target region comprises a region of the parasympathetic nervous system, the electrical impulse being sufficient to modulate one or more nerves within the region.

15. The method of claim 13 wherein the electrical impulse has a frequency of between about 15 Hz to 25 Hz, an amplitude of between about 0.2 to 20 volts and a pulsed-on time of between about 200 to 400 microseconds.

16. The method of claim 14 wherein the electrical impulse is sufficient to inhibit an activity of the region of the parasympathetic nervous system.

17. The method of claim 14 wherein the electrical impulse is sufficient to stimulate an activity of the region of the parasympathetic nervous system.

18. The method of claim 13 wherein the disorder is hypotension.

19. The method of claim 13 wherein the disorder is hypotension associated with shock.

20. A device for the treatment of a patient with a disorder comprising:
   an electrical impulse generator;
   one or more electrodes coupled to the electrical impulse generator; and
   wherein the electrical impulse generator is configured for generation of an electrical impulse having a frequency of about 10 to 50 Hz and suitable for increasing blood pressure when the electrical impulse is applied to a target region comprising parasympathetic nerves in the patient.

21. The device of claim 20 wherein the frequency is between about 15 to 30 Hz.

22. The device of claim 20 wherein the frequency is about 25 Hz.

23. The device of claim 20 wherein the electrical impulse has an amplitude of between about 0.2 to 20 volts.

24. The device of claim 20 wherein the electrical impulse has an amplitude of between about 1 volt to 1.5 volts.

25. The device of claim 20 wherein the electrical impulse has a pulsed-on time of between about 200-400 microseconds.

26. The device of claim 20 wherein the electrical impulse has a pulsed-on time of about 200 microseconds.

27. The device of claim 20 wherein the target region comprises a region of the parasympathetic nervous system.

28. The device of claim 27 wherein the target region comprises a region of the vagus nerve proximal to the cardiac branch of the vagus nerve.

29. The device of claim 20 wherein the electrical impulse is sufficient to increase blood pressure and maintain a stable heart rate.

30. The device of claim 20 wherein the disorder is hypotension.

31. The device of claim 20 wherein the disorder is hypotension associated with shock.

32. The device of claim 27 wherein the electrical impulse is sufficient to inhibit an activity of the region of the parasympathetic nervous system.

33. The device of claim 27 wherein the electrical impulse is sufficient to stimulate an activity of the region of the parasympathetic nervous system.

* * * * *